United States Patent [19]

Molloy et al.

[11] 4,395,410

[45] Jul. 26, 1983

[54] QUATERNARY AMMONIUM ANTIARRHYTHMIC DRUGS

[75] Inventors: Bryan B. Molloy, North Salem; Mitchell I. Steinberg, Indianapolis, both of Ind.

[73] Assignee: Eli Lilly and Company, Indianapolis, Ind.

[21] Appl. No.: 273,822

[22] Filed: Jun. 15, 1981

Related U.S. Application Data

[60] Division of Ser. No. 102,043, Dec. 10, 1979, Pat. No. 4,289,787, which is a continuation-in-part of Ser. No. 861,789, Dec. 19, 1977, abandoned.

[51] Int. Cl.³ .................. A61K 31/33; A61K 31/445; C07D 207/04; A61K 31/40
[52] U.S. Cl. ................ 424/244; 260/239 B; 424/267; 424/274; 546/192; 548/570; 548/566; 548/578
[58] Field of Search ............... 424/244, 267, 274; 260/239 B, 326.87; 546/192

[56] References Cited

U.S. PATENT DOCUMENTS

| | | | |
|---|---|---|---|
| 2,592,191 | 4/1952 | Ruddy | 260/326.87 |
| 2,884,436 | 4/1959 | Janssen et al. | 260/457 |
| 3,037,910 | 6/1962 | Copp et al. | 260/326.87 |
| 3,972,935 | 8/1976 | Molly | 424/329 |
| 4,001,433 | 1/1977 | Maxwell et al. | 424/329 |
| 4,034,011 | 7/1977 | Molly | 260/567.6 M |
| 4,277,471 | 7/1981 | Lacefield et al. | 546/192 |

FOREIGN PATENT DOCUMENTS 1157541 7/1969 United Kingdom ............... 546/192

OTHER PUBLICATIONS

Chem. Abst. 92, 110,643u (1980)–Molloy et al.
Pharmac. 37, 555–584 (1969)–Barlow et al.
European J. of Pharm. 35, 245–252 (1976)–Lien et al.
Chem. Abst. 54, 19588(f) (1960)–Morikawa.

Primary Examiner—Douglas W. Robinson
Attorney, Agent, or Firm—Charles W. Ashbrook; Arthur R. Whale

[57] ABSTRACT

Quaternary ammonium salts of certain phenylpropylamines and phenylbutylamines are useful antiarrhythmic drugs. A method for treating arrhythmia and prolonging the action potential of cardiac tissue is provided. Pharmaceutical formulations containing such quaternary ammonium salts are disclosed.

13 Claims, No Drawings

QUATERNARY AMMONIUM ANTIARRHYTHMIC DRUGS

CROSS-REFERENCE TO RELATED APPLICATIONS

This is a division of Ser. No. 102,043 filed Dec. 10, 1979, now U.S. Pat. No. 4,289,787, which was a continuation-in-part of Ser. No. 861,789, filed Dec. 19, 1977 now abandoned.

BACKGROUND OF THE INVENTION

Despite the extensive amount of research and the relatively large number of drugs devoted to the treatment of heart disease, mortality from cardiovascular disorders remains alarmingly high. Cardiovascular deterioration is known to commence early in life and is progressive throughout. It has been said that about half the population by the age of 50 have about fifty percent occlusion of at least one coronary artery, while less than about one-fifth have entirely unoccluded arteries at this age, Rissanen, *Advan. Cardiol.*, 4, 99 (1970).

The mechanism of action of various antiarrhythmic drugs generally is mediated by their effects upon the electrophysiological properties of cardiac muscle and conducting tissue. The electrical potential difference present in a heart muscle is created by ionic concentration differences across the membrane of the cardiac cell; the cardiac membrane being selectively permeable to different ionic species which pass through pores or channels. When the cardiac muscle is at rest, its interior is negatively charged due to a high intracellular concentration of non-diffusable large anions. During the action potential, the interior becomes positively charged relative to the exterior due to the sudden increase in sodium permeability resulting in the influx of positive charges. Then, until repolarization of the tissue takes place, the membranes are totally refractory to the passage of further sodium ions. The refractory period is quite long since repolarization is about 100 times slower than depolarization. Any drug which shortens the duration of the cardiac action potential thus necessarily shortens the refractory period and consequently increases the possibility of re-entrant rhythms under certain abnormal conditions. The refractory period would of course be prolonged if repolarization were delayed.

Various drugs have been used in the treatment of rhythm disorders. Quinidine, procaine amide, and lidocaine are perhaps among the best known and most widely used agents. All of such drugs act primarily by directly affecting membrane conductance so as to increase or decrease various ionic flows. A number of quaternary ammonium salts recently have been found useful in treating arrhythmia. Among such salts is a drug called bretylium (see U.S. Pat. No. 3,038,004). Bretylium is a salt of (o-bromobenzyl)ethyldimethylammonium cation. It has been shown to be effective in the treatment of disturbances of ventricular rhythm which are not successfully treated by other more conventional drugs, see Morgan et al., *J. Pharm. Sci.*, 65, 467 (1976). Unfortunately, it possesses many adverse side effects including sympathomimetic and sympathomlytic effects.

Several investigators recently have been interested in developing quaternary ammonium compounds which are useful antiarrhythmic and antifibrillatory drugs which at the same time cause no adverse effects on the antonomic nervous system (see particularly Lucchesi et al., "Pharmacological Modification of Arrhythmias After Experimentally Induced Acute Myocardial Infarction" American Heart Association Monograph No. 47, December, 1975). The dimethyl quaternary ammonium salt of propranolol has demonstrated useful antiarrhythmic activity against a variety of experimentally induced cardiac arrhythmias, Schuster, et al., *J. Pharmacol, Exp. Ther.,* 184, 213 (1973) and Kniffen et al., *J. Pharmacol. Exp. Ther.,* 187, 260 (1973).

An object of this invention is to provide certain phenylbutyl ammonium salts and phenylpropyl ammonium salts which are extremely potent in prolonging cardiac action potential duration. The compounds are thus useful for prolonging the refractory period in cardiac muscle and conducting tissue and thereby are useful in decreasing the vulnerability of the heart to re-entrant arrhythmias.

SUMMARY OF THE INVENTION

This invention relates to specific and potent antiarrhythmic drugs which are useful in preventing ventricular fibrillation and other re-entrant arrhythmias by selectively prolonging the action potential, and consequently the refractoriness, of cardiac tissue. The invention additionally is directed to a method of prolonging the action potential of cardiac tissue and thus preventing and treating ventricular fibrillation and related re-entrant arrhythmias. The invention also provides pharmaceutical formulations useful in the treatment of cardiac arrhythmia.

The decrease in the rate of rise of the action potential caused by many of the commonly used cardiovascular drug results in conduction depression in the intact heart. This action, in conjunction with the shortened refractory period, may predispose the heart to a variety of re-entrant arrhythmias, including ventricular fibrillation and flutter, the most serious forms of arrhythmia.

The compounds of this invention are particularly potent in prolonging both the action potential and refractory period of cardiac tissue. Moreover, they are selective in their activity in that they cause no inhibition of the rate of rise of the action potential at concentrations that prolong refractoriness. The compounds of this invention therefore are useful in the treatment and prevention of a variety of arrhythmias which have as their basis single or multiple re-entrant rhythms. The compounds typically will be used in the treatment of arrhythmias such as ventricular flutter, ventricular fibrillation, ventricular pre-excitation, atrial fibrillation, and supraventricular tachycardia.

In one embodiment of the invention there is provided a method of treating re-entrant arrhythmias and preventing the development thereof in humans which comprises administering to a subject suffering from such arrhythmia and in need of treatment or to a subject suspected of developing a re-entrant arrhythmia an antiarrhythmically effective dose of a compound having the general formula

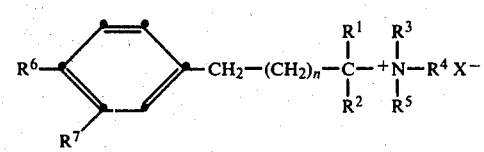

wherein:

n is 1 or 2;
$R^1$ is hydrogen or $C_1-C_2$ alkyl;
$R^2$ is hydrogen or $C_1-C_3$ alkyl;
$R^3$ is $C_1-C_4$ alkyl or phenyl $C_1-C_4$ alkyl;
$R^4$ is $C_1-C_8$ alkyl;
$R^5$ is $C_1-C_{10}$ alkyl, or $R^4$ and $R^5$ taken together with the adjacent nitrogen to which they are attached complete a heterocyclic ring having 4 to 7 carbon atoms;
$R^6$ and $R^7$ independently are hydrogen, hydroxy, halogen, nitro, $C_1-C_3$ alkoxy, or $C_1-C_3$ alkyl, provided that at least one of $R^6$ and $R^7$ is hydrogen; and
X is a therapeutically acceptable anion.

A preferred method of treatment according to this invention comprises administering a compound of the above formula wherein $R^3$ is $C_1-C_4$ alkyl and wherein $R^6$ and $R^7$ independently are hydrogen, halogen, nitro, $C_1-C_3$ alkoxy, or $C_1-C_3$ alkyl.

This invention particularly provides a method of preventing the development of ventricular fibrillation in humans comprising administering an effective dose of a compound having the above formula wherein:
n is 2;
$R^1$ is hydrogen or methyl;
$R^2$ is hydrogen;
$R^3$ is $C_1-C_2$ alkyl;
$R^4$ is $C_1-C_2$ alkyl;
$R^5$ is $C_5-C_8$ alkyl; and
$R^6$ is other than hydrogen.

An especially preferred method of treating conditions of ventricular fibrillation according to this invention comprises administering an antiarrhythmically effective dose of N,N-diethyl-N-n-heptyl-4-(4-chlorophenyl)-butylammonium, wherein the anion is pharmaceutically acceptable, such as chloride, bromide, or preferably phosphate. The latter compound, namely N,N-diethyl-N-n-heptyl-4-(4-chlorophenyl)butylammonium phosphate, has now been shown to be a particularly potent antifibrillatory agent, and now is generically referred to as clofilium.

This invention additionally comprehends a pharmaceutical formulation useful in the treatment of ventricular fibrillation and other re-entrant arrhythmias comprising a compound having the above general formula wherein:
n is 1 or 2;
$R^1$ is hydrogen or $C_1-C_2$ alkyl;
$R^2$ is hydrogen or $C_1-C_3$ alkyl;
$R^3$ is $C_1-C_4$ alkyl or phenyl $C_1-C_4$ alkyl;
$R^4$ is $C_1-C_8$ alkyl;
$R^5$ is $C_1-C_{10}$ alkyl, or $R^4$ and $R^5$ taken together with the adjacent nitrogen atom to which they are attached complete a heterocyclic ring having 4 to 7 carbon atoms;
$R^6$ and $R^7$ independently are hydrogen, hydroxy, halogen, nitro, $C_1-C_3$ alkoxy, or $C_1-C_3$ alkyl; provided that at least one of $R^6$ and $R^7$ is hydrogen; and
X is a therapeutically acceptable anion, in association with a pharmaceutical diluent or carrier therefor.

A preferred formulation is one comprising a compound of the above formula wherein $R^3$ is $C_1-C_4$ alkyl and wherein $R^6$ and $R^7$ independently are hydrogen, halogen, nitro, $C_1-C_3$ alkoxy, or $C_1-C_3$ alkyl, in association with a carrier therefor.

A more preferred formulation according to this invention comprises a compound having the above general formula wherein:
n is 2;
$R^1$ is hydrogen or $C_1-C_2$ alkyl;
$R^2$ is hydrogen;
$R^3$ is $C_1-C_2$ alkyl;
$R^4$ is $C_1-C_2$ alkyl;
$R^5$ is $C_5-C_8$ alkyl; and
$R^6$ is other than hydrogen, in association with a suitable carrier therefor.

A particularly preferred formulation comprises as active ingredient an effective amount of either N,N-diethyl-N-n-hepty-4-(4-chlorophenyl)butylammonium bromide or clofilium, the corresponding phosphate salt.

A further embodiment of this invention comprises a compound having the above general formula wherein:
n is 1 or 2;
$R^1$ is hydrogen or $C_1-C_2$ alkyl;
$R^2$ is hydrogen or $C_1-C_3$ alkyl;
$R^3$ is $C_1-C_4$ alkyl or phenyl $C_1-C_4$ alkyl;
$R^4$ is $C_1-C_8$ alkyl;
$R^5$ is $C_1-C_{10}$ alkyl, or $R^4$ and $R^5$ taken together with the adjacent nitrogen to which they are attached complete a heterocyclic ring having 4 to 7 carbon atoms;
$R^6$ and $R^7$ independently are hydrogen, hydroxy, halogen, nitro, $C_1-C_3$ alkoxy, or $C_1-C_3$ alkyl, provided that at least one of $R^6$ and $R^7$ is hydrogen, and when n is 1 and $R^6$ and $R^7$ independently are other than nitro, $R^5$ is $C_6-C_{10}$ alkyl; and
X is a therapeutically acceptable anion.

A preferred group of compounds are those defined as above wherein $R^3$ is $C_1-C_4$ alkyl and $R^6$ and $R^7$ independently are hydrogen, halogen, nitro, $C_1-C_3$ alkoxy, or $C_1-C_3$ alkyl.

Additionally preferred compounds have the above formula wherein $R^5$ is $C_5-C_8$ alkyl.

A further class of compounds are those of the above formula wherein $R^6$ is other than hydrogen, most preferably halogen or nitro.

Another preferred group of compounds have the above formula wherein n is 2.

Additionally preferred classes of compounds embodied by this invention are those of the above general formula having one or more of the following characteristics:

1. n is 2 and $R^6$ is halogen or nitro.
2. $R^3$ and $R^4$ both are $C_1-C_2$ alkyl and $R^5$ is $C_3-C_{10}$ alkyl, ideally $C_5-C_8$ alkyl.
3. $R^3$ and $R^4$ both are methyl and $R^5$ is n-hexyl.
4. $R^3$ and $R^4$ both are methyl and $R^5$ is n-heptyl.
5. $R^3$ and $R^4$ both are ethyl and $R^5$ is n-hexyl or n-heptyl.
6. $R^3$ is $C_1-C_2$ alkyl and $R^4$ and $R^5$ are $C_4-C_5$ alkyl.
7. $R^1$ is $C_1-C_2$ alkyl and $R^2$ is hydrogen.
8. $R^1$ is methyl and $R^2$ is hydrogen.
9. n is 2, $R^1$ is methyl, $R^2$ is hydrogen, $R^3$ and $R^4$ are $C_1-C_2$ alkyl, $R^5$ is $C_6-C_7$ alkyl, and $R^6$ is other than hydrogen.
10. n is 2, $R^1$ is methyl, $R^2$ is hydrogen, $R^3$ is $C_1-C_2$ alkyl, $R^4$ and $R^5$ are $C_4-C_5$ alkyl, and $R^6$ is other than hydrogen.
11. n is 2, $R^1$ and $R^2$ are hydrogen, $R^3$ and $R^4$ independently are $C_1-C_2$ alkyl, $R^5$ is $C_5-C_8$ alkyl, $R^6$ is halogen or nitro, and $X^-$ is phosphate.

In all of the above preferred groups, it is most desirable that $R^3$, $R^4$ and $R^5$ are normal alkyl chains.

Preferred anions defined in the above formula by "$X^-$" include halide, especially chloride and bromide, as well as phosphate.

A particularly preferred compound defined by the above formula is N,N-diethyl-N-n-heptyl-4-(4-chlorophenyl)butylammonium phosphate, now known generically as clofilium.

DETAILED DESCRIPTION OF THE INVENTION

In the above formula $R^1$ represents hydrogen or a $C_1$–$C_2$ alkyl group, namely methyl and ethyl. $R^2$ represents hydrogen as well as $C_1$–$C_3$ alkyl such as methyl, ethyl, isopropyl and n-propyl. $R^3$ defines a $C_1$–$C_4$ alkyl group such as methyl, ethyl, n-propyl, n-butyl and isopropyl. $R^3$ additionally defines a phenyl $C_1$–$C_4$ alkyl group, for example benzyl, 2-phenylethyl, 3-phenylpropyl, 2-phenylbutyl, and the like. $R^4$ defines a $C_1$–$C_8$ alkyl group. Such term includes groups such as methyl, ethyl, n-propyl, n-butyl, isopentyl, 2-methylbutyl, 2-methylpentyl, 1-ethylpentyl, n-heptyl, n-octyl, isooctyl, and the like. Similarly, $R^5$ represents $C_1$–$C_{10}$ alkyl such as methyl, ethyl, n-pentyl, isohexyl, 2-ethylheptyl, n-heptyl, 3-methylheptyl, 1,2-dimethylheptyl, 1,2-dimethyloctyl, 1,1-dimethylheptyl, n-nonyl, n-decyl, and related alkyl groups. Preferred $R^4$ and $R^5$ alkyl groups are straight claim alkyl groups such as n-pentyl and n-heptyl.

In addition to $R^4$ and $R^5$ each defining an alkyl group, $R^4$ and $R^5$ can be taken together with the adjacent nitrogen to which they are attached to complete a heterocyclic ring containing from 4 to 7 carbon atoms. Examples of such ring systems include pyrrolidine, piperidine, hexahydroazepine and octahydroazocine.

As noted hereinabove, $R^6$ and $R^7$ are selected from hydrogen, hydroxy, halogen, $C_1$–$C_3$ alkoxy, nitro, and $C_1$–$C_3$ alkyl. Typical halogen groups are fluorine, chlorine and bromine. Examples of $C_1$–$C_3$ alkoxy groups include methoxy, ethoxy and isopropoxy. $C_1$–$C_3$ alkyl groups include methyl, ethyl, and n-propyl.

The compounds of this invention are quaternary ammonium salts and as such require an anion, defined in the above formula by "$X^-$". Any suitable anion which goes together with the ammonium cation to form a therapeutically acceptable salt can be utilized. Commonly used anions include chloride, bromide, sulfonate, p-toluenesulfonate, methanesulfonate, p-bromophenylsulfonate, phosphate, carbonate, oxalate, succinate, citrate, benzoate, acetate, and the like. A preferred and commonly used anion is bromide. Another preferred anion is phosphate.

The phenylpropylammonium salts and phenylbutylammonium salts of this invention can be prepared by any of a number of art recognized chemical processes. Generally, an N,N-dialkyl-3-phenylpropylamine or N,N-dialkyl 4-phenylbutylamine will simply be reacted with about an equimolar quantity or an excess of an alkylating agent such as an alkyl halide, alkyl sulfate, alkyl tosylate, or the like. More particularly, an N,N-disubstituted propyl or butylamine of the formula

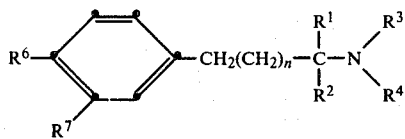

can be reacted with an alkylating agent of the formula $R^5$—X in a solvent such as diethyl ether. The quaternary ammonium salts prepared by any of the methods discussed herein characteristically exist as highly crystalline white solids. Generally, when a tertiary amine and an alkylating agent are reacted as described above, the product salt precipitates out of solution and can accordingly be recovered by filtration. The salt so formed can be readily purified further if desired by conventional methods such as recrystallization, utilizing common organic solvents such as ethyl acetate, acetone, methanol, benzene, and the like.

An alternative method for preparing the quaternary ammonium salts of this invention comprises reacting a tertiary amine with a phenylpropyl or phenylbutyl derivative which bears a good leaving group at the 1-position. Good leaving groups are well known to those skilled in the art and include groups such as chloro, bromo, methanesulfonyl, p-toluenesulfonyl, azide, and the like. A preparation according to this latter method comprises reacting a tertiary amine such as methyl ethyl n-octylamine with about an equimolar quantity of a phenylpropyl derivative such as 3-(3-bromophenyl)propyl chloride or a phenylbutyl derivative such as 4-(4-methoxyphenyl)butyl bromide. Such condensation generally is carried out in an unreactive solvent such as diethyl ether or benzene, or if preferred the reaction can be carried out neat. The condensation typically is substantially complete within 1 to 10 days when carried out at a temperature of about 50° to 200° C. The product, a quaternary ammonium salt, normally is crystalline and can be recovered by filtration and recrystallized if desired.

A preferred group of compounds according to this invention are those phenylpropylammonium salts and phenylbutylammonium salts wherein one of the alkyl substituents on the ammonium nitrogen atom is lower alkyl such as methyl or ethyl. A particularly preferred method for preparing such compounds comprises simply adding the appropriate tertiary amine to a solution which is saturated with a methyl or ethyl alkylating agent such as a halide. For example, solvents such as diethyl ether, diisopropyl ether, ethylacetate, acetonitrile and the like are readily saturated with an alkylating agent such as methyl bromide or ethyl chloride. When a tertiary amide is added to such solution, quaternization generally is effected very rapidly to produce the corresponding salt as a solid precipitate.

Phenylpropyl and phenylbutyl ammonium salts of the above general formula which bear a hydroxy substituent in the phanyl ring (i.e. $R^6$ or $R^7$ is hydroxy) are conveniently prepared by de-etherification of a corresponding phenylpropyl or phenylbutyl compound wherein $R^6$ or $R^7$ is methoxy. For example, a compound such as N,N-diethyl-N-n-pentyl-4-(4-methoxyphenyl)-butylammonium hydroxide can be reacted with glacial acetic acid and hydrobromic acid to effect removal of a methyl group and thus provide N,N-diethyl-N-n-pentyl-4-(4-hydroxyphenyl)butylammonium hydroxide.

The anion associated with the quaternary ammonium cationic portion of the salts of this invention is defined in the above formula by $X^-$. It should be recognized that the particular anion forming a part of any salt of this invention is not of a critical nature, so long as the salt as a whole is pharmacologically acceptable and as long as the anionic moiety does not contribute numerous undesired qualities to the salt as a whole. Preferred anions to be utilized are the halides, and whenever a halide such as chloride or bromide is the anion portion of the salt, it can, if desired for any reason, be readily replaced by a different anion. Such replacement can be effected either directly by metathesis, i.e., by double decomposition either in solution or by employing an ion exchange resin, or alternatively by conversion of the quaternary salt to the corresponding hydroxide, and then neutralization of the hydroxide by reaction with the appropriate acid. For example, a quaternary ammonium halide can be passed over a hydroxide ion exchange resin, or reacted with aqueous silver oxide, to form the corresponding quaternary ammonium hydroxide. Reaction of the hydroxide with an acid such as methanesulfonic acid, formic acid, butyric acid, nitric acid, phosphoric acid or the like, then provides the quaternary ammonium salt having an anion corresponding to the acid utilized. As a typical illustration, a compound of the invention such as N,N-diethyl-N-n-heptyl-4-(4-chlorophenyl)butylammonium chloride can be dissolved in water and passed over a suitable ion-exchange resin, for instance a Dowex 1-X8 hydroxide resin, to form the corresponding N,N-diethyl-N-n-heptyl-4-(4-chlorophenyl)butylammonium hydroxide. Reaction of the latter compound with an acid such as phosphoric acid then provides N,N-diethyl-N-n-heptyl-4-(4-chlorophenyl)butylammonium phosphate.

The starting materials required for the synthesis of the salts of this invention are by and large known compounds, or are readily available by known procedures. As hereinabove pointed out, a preferred procedure for preparing quaternary ammonium salts comprises reacting a tertiary amine with an alkylating agent. The required tertiary amines can be prepared by any of a number of methods. For example, a phenylpropyl halide or phenylbutyl halide can be reacted with a primary amine such as n-octylamine or isopentylamine to provide the corresponding secondary amine. The secondary amine can then be reacted with an alkylating agent to give the corresponding tertiary amine. When a tertiary amine wherein one of the alkyl groups is methyl is desired, a particularly convenient method of preparation comprises reacting the appropriate primary or secondary amine with formaldehyde and formic acid. Primary and secondary amines are additionally readily prepared by reduction of an appropriate phenylalkyl amide. For example, reduction of an amide such as N-n-heptyl-3-(3-nitrophenyl)propionamide affords the corresponding N-n-heptyl-3-(3-nitrophenyl)propylamine. Reaction of the latter compound with formaldehyde and formic acid affords N-methyl-N-n-heptyl-3-(3-nitrophenyl)-propylamine.

Still another method for preparing amine starting materials is by reductive amination of ketones. For example, the starting materials needed to prepare salts having the above formula wherein $R^1$ is hydrogen and $R^2$ is $C_1$–$C_3$ alkyl are best prepared by a procedure which comprises reacting a primary amine, i.e., an amine of the formula $R_5NH_2$, with a phenylethyl or phenylpropyl $C_1$–$C_3$ alkyl ketone. For instance, a ketone such as 2-phenylethyl n-propyl ketone can be reacted with isooctylamine in the presence of hydrogen and a suitable catalyst such as palladium on carbon to effect condensation and reduction to provide N-isooctyl-1-n-propyl-3-phenylpropylamine. Further alkylation and quaternization of such amine provides a compound of this invention.

The following list of quaternary ammonium salts is illustrative of the compounds comprehended by this invention.

N-Ethyl-N-methyl-N-isopropyl-4-phenylbutylammonium chloride;

N,N-Di-n-propyl-N-n-octyl-3-(4-isopropylphenyl)-propylammonium methanesulfonate;

N-Ethyl-N-n-heptyl-N-n-octyl-1,1-diethyl-3-(3-ethoxyphenyl)propylammonium fluoride;

N,N-Di-n-octyl-N-isopropyl-4-(3-fluorophenyl)-butylammonium acetate;

N,N,N-Tri-n-propyl-1-ethyl-4-phenylbutylammonium succinate;

N-n-Propyl-N-n-hexyl-N-(3-methylheptyl)-4-(3-ethylphenyl)butylammonium tartrate;

N,N-Di-n-butyl-N-(3-ethylheptyl)-1-ethyl-1-methyl-3-(3-ethoxyphenyl)propylammonium benzenesulfonate;

N-Ethyl-N-isobutyl-N-n-nonyl-4-(3-nitrophenyl)-butylammonium fluoride;

N-Methyl-N-(3-ethylpentyl)-N-(3-methyloctyl)-1,1-diethyl-4-(3-bromophenyl)butylammonium p-toluenesulfonate;

N,N-Diethyl-N-n-heptyl-4-phenylbutylammonium iodide;

N-Ethyl-4-phenylbutylpyrrolidinium butyrate;

N-n-Butyl-3-(3-ethoxyphenyl)propylpiperidinium oxalate;

N-Ethyl-4-(4-n-propoxyphenyl)butylhexahydroazepinium chloride;

N,N-Diethyl-N-n-hexyl-3-phenylpropylammonium bromide;

N,N-Diethyl-N-n-decyl-3-(4-hydroxyphenyl)-propylammonium bromide;

N-Ethyl-4-phenyloctahydroazocinium hydroxide;

N,N-Di-(2-methylheptyl)-N-n-propyl-1,1-diethyl-4-(3-methoxyphenyl)butylammonium bromide;

N,N-Di-n-propyl-N-n-octyl-1-ethyl-1-methyl-3-(4-ethoxypheny)propylammonium fluoride;

N-Benzyl-N-n-octyl-N-n-propyl-1-ethyl-1-n-propyl-3-(3-nitrophenyl)propylammonium phosphate;

N,N-Di-n-pentyl-N-ethyl-1-methyl-4-(3-iodophenyl)-butylammonium benzenesulfonate; and N,N-Diethyl-N-n-heptyl-4-(4-fluorophenyl)butylammonium methanesulfonate.

It should be noted that certain of the compounds of this invention have an asymmetric center and accordingly exist as optical isomers. For example, compounds of the above formula wherein $R^1$ and $R^2$ are different exist as a d-isomer, an l-isomer, and as the racemic mixture. Such compounds generally are utilized as a racemic mixture, however separation of such mixture into the optically active isomers can be readily accomplished if desired. Such separation is accomplished by forming a diastereomer by reaction of an amine precursor with an optically active substrate, separating the diastereomers by routine methods such as crystallization, and then cleaving the optically active substrate. A typical resolution, for instance, comprises reacting an amine such as dl-1-ethyl-3-phenylpropylamine with optically active d or l α-methylbenzyl bromide. Repeated crystallization of the product to provide the separated diastereomers, followed by de-benzylation by hydrogenolysis, provides optically active d and l 1-ethyl-3-phenylpropylamine. The latter compound can then be alkylated and quaternized by the methods hereinabove described.

As already pointed out, the compounds of this invention are useful in treating and preventing re-entrant arrhythmias and are particularly important due to their potent and selective ability to prolong the action potential duration of cardiac tissue. The compounds of the invention accordingly are useful in the treatment of arrhythmia by decreasing the vulnerability of the heart to re-entrant rhythms and ventricular fibrillation by prolonging the time of electrical systole. The activity of the compounds of this invention has been analyzed by utilizing standard electrophysiological techniques to measure resting potential, action potential amplitude, duration, rate of rise and effective refractory periods of normal canine Purkinje fibers superfused in vitro with Ringer solution at 35° C. and stimulated at 1 Hz. For example, N,N-diethyl-N-n-heptyl-4-(4-chlorophenyl)-butylammonium bromide, at a concentration of $2 \times 10^{-8}$ molar, effected a twenty percent prolongation of action potential duration in Purkinje fibers that were driven at a constant frequency of 1 Hz. Similarly, N,N-dimethyl-N-n-heptyl-1-methyl-4-phenylbutylammonium bromide caused a twenty-five percent prolongation under the same conditions.

In addition to demonstrating in vitro utility in prolonging action potential duration and refractoriness, certain compounds comprehended by this invention also have been examined in the intact dog. In a typical experiment utilizing dogs subjected to electrically-induced ventricular fibrillation, a marked decrease in the vulnerability of the heart to fibrillation was observed when doses from about 0.1 μmole/kg. of body weight to about 50 μmole/kg. were administered prior to the induction of fibrillation. The compounds of this invention also have been shown to convert flutter, ventricular fibrillation, or rapid tachycardia, experimentally established both in vitro and in vivo, to a normal sinus rate as a result of the prolongation of refractoriness. Such actions demonstrate that the compounds of this invention are useful in situations where rapid inappropriate ventricular rates are present, particularly in cases of ventricular pre-excitation tachyarrhythmia.

There is also provided by this invention a method for treating arrhythmia which comprises administering to a subject suffering from an arrhythmia and in need of treatment or to a subject suspected of developing an arrhythmia an effective amount for treating such arrhythmia of a compound of this invention. The compounds are preferably utilized for the control of reentrant arrhythmias in humans and for the prevention of sudden death resulting from ventricular fibrillation. Accordingly it is contemplated that the compounds are best utilized in a prophylactic treatment. Moreover, since the compounds enhance the electrical stability of the heart, they can be used in conjunction with electrical devices designed to terminate cardiac arrhythmias such as ventricular tachycardia and ventricular fibrillation.

The compounds can be administered either orally or parenterally, and for prophylactic treatment are best formulated for convenient oral administration. The particular dose of compound administered according to this invention will of course be determined by the particular circumstances surrounding the case, including the compound administered, the route of administration, the particular arrhythmia being treated, and similar considerations. A typical dose for prophylactic treatment, however, will contain from about 50 μg/kg. to about 500 μg/kg. of the active compound of this invention when administered orally. For I.V. administration, the dose will be from about 20 μg/kg. to about 400 μg/kg, preferably about 20 to about 200 μg/kg.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. A gelatin capsule suited to oral adminstration for prophylactic treatment of heart disease may contain, for example, a compound of this invention such as N,N-diethyl-N-n-heptyl-4-(4-nitrophenyl)butylammonium bromide in the amount of about 1 to about 5 mg. Such formulation can be administered orally at the rate of about 1 or 2 capsules per day or more often as needed depending upon the particular condition and patient being treated.

For parenteral administration, a compound of this invention can be formulated for intramuscular or intravenous administration. In the case of treatment of a patient suffering from a severe cardiac arrhythmia, it may be desirable to administer a compound of the invention by intravenous infusion in order to effect a speedy conversion to a normal sinus rhythm. Such normal condition can then be maintained by oral administration.

For parenteral administration, the compounds of this invention are formulated with any of a number of pharmaceutically acceptable carriers and diluents to constitute an injectable liquid solution. Commonly used diluents and carriers include water or saline solution, buffered aqueous solutions, as well as dispersing and surface active agents if needed. It will also be noted that a compound of this invention can be administered in combination with other known antiarrhythmic drugs which have potent antiautomatic effects. Such drugs include aprindine, quinidine, propranolol and the like. A typical formulation suited to intramuscular administration may contain a compound of this invention such as N,N-di-n-pentyl-N-n-propyl-4-phenylbutylammonium methanesulfonate in the amount of about 1.0 to 25.0 mg., with or without another antiarrhythmic drug such as quinidine in the amount of about 100 to 200 mg., and a suitable solubilizing agent and sufficient sterile water to bring the volume to about 2 ml. Such formulation can be injected at a rate of 1 to 4 times per day or more often depending upon the particular condition of the patient being treated.

The present invention will now be more fully described in terms of typical working examples. The following discussions are to be taken as illustrative of the compounds comprehended by the invention, and are not to be construed as limiting the invention in any particular aspect.

EXAMPLE 1

N-(n-nonyl)-4-phenylbutylamine

A solution of 30 g. of 4-phenylbutyl chloride and 77 g. of n-nonylamine was heated at 100° C. for forty-eight hours. The reaction mixture was cooled and added to 5000 ml. of water. The aqueous reaction mixture was then made alkaline by the addition of 5 N sodium hydroxide solution. The aqueous alkaline solution was extracted several times with diethyl ether and the ethereal extracts were combined and the solvent removed therefrom by evaporation under reduced pressure to afford an oil. The oil was distilled to provide 30.2 g. of N-(n-nonyl)-4-phenylbutylamine.

EXAMPLE 2

N-(n-nonyl)-N-methyl-4-phenylbutylamine

To a cold (5° C.) solution of 28.2 ml. of ninety percent aqueous formic acid was added portionwise over 10 minutes a solution of 30.2 g. of N-(n-nonyl)-4-phenylbutylamine and 27 ml. of thirty-seven percent aqueous formaldehyde. The reaction mixture was stirred and heated at 100° C. for twelve hours. The reaction mixture then was cooled to 25° C. and acidified by the addition of 90 ml. of 4 N hydrochloric acid. The acidic solution was concentrated to a volume of about 20 ml. The mixture next was diluted with water and the aqueous acidic solution was washed with diethyl ether and then made alkaline by the addition of 5 N sodium hydroxide. The aqueous alkaline solution was extracted three times with 100 ml. portions of diethyl ether. The ethereal extracts were combined, washed with water and dried. Evaporation of the solvent under reduced pressure provided 30.16 g. of the product as an oil. The oil thus formed was distilled to afford 24.99 g. of N-(n-nonyl)-N-methyl-4-phenylbutylamine. B.P. 124°–127° C. at 0.01 torr.

EXAMPLE 3

N-(n-nonyl)-N-methyl-4-phenylbutylammonium oxalate

To a stirred solution of 24.99 g. of N-(n-nonyl)-N-methyl-4-phenylbutylamine in about 300 ml. of isopropyl alcohol was added in one portion 7.8 g. of oxalic acid in 120 ml. of isopropyl alcohol. The product crystallized out of solution and collected by filtration to provide 23.9 g. of N-(n-nonyl)-N-methyl-4-phenylbutylammonium oxalate. M.P. 118°–120° C.

Analysis calc. for $C_{22}H_{37}NO_4$ Theory: C, 69.62; H, 9.83; N, 3.69. Found: C, 69.81; L H, 9.60; N, 3.89.

EXAMPLE 4

N,N-Dimethyl-N-(n-nonyl)-4-phenylbutylammonium bromide

Seven grams of N-(n-nonyl)-N-methyl-4-phenylbutylammonium oxalate was suspended in diethyl ether and reacted with 5 N sodium hydroxide solution. The organic layer was separated and the solvent was evaporated therefrom to provide 5.3 g. of N-(n-nonyl)-N-methyl-4-phenylbutylamine. The latter compound was dissolved in 150 ml. of diethyl ether and the solution was stirred at 25° C. in a flask equipped with a drying tube packed with calcium sulfate. The ethereal solution was saturated with methyl bromide gas, and the mixture was stored at room temperature for forty-eight hours. The solid precipitate which had formed was collected by filtration and was recrystallized from 50 ml. of ethyl acetate and 80 ml. of cyclohexane. The crystalline product was collected by filtration and dried in a desiccator to provide 2.27 g. of N,N-dimethyl-N-(n-nonyl)-B 4-phenylbutylammonium bromide. M.P. 59°–61° C.

Analysis calc. for $C_{21}H_{38}BrN$ Theory: C, 65.61; H, 9.96; N, 3.64; Br, 20.78. Found: C, 65.94; H, 9.82; L N, 3.68; Br, 20.55.

EXAMPLES 5–24

The following compounds were prepared by reacting a tertiary amine with an alkyl bromide according to the procedure described in Example 4.

N,N-di-n-heptyl-N-methyl-4-phenylbutylammonium bromide M.P. 84°–86° C.

Analysis calc. for $C_{25}H_{46}BrN$ Theory: C, 68.16; H, 10.52; N, 3.18; Br, 18.14. Found: C, 67.88; H, 10.56; N, 3.27; Br, 18.01.

N,N-dimethyl-N-n-octyl-4-phenylbutylammonium bromide M.P. 47°–50° C.

Analysis calc. for $C_{20}H_{36}BrN$ Theory: C, 64.85; H, 9.80; N, 3.78; Br, 21.57. Found: C, 64.67; H, 9.51; N, 3.56; Br, 21.49.

N,N-di-n-hexyl-N-methyl-4-phenylbutylammonium bromide M.P. 65°–67° C.

Analysis calc. for $C_{23}H_{42}BrN$ Theory: C, 66.97; H, 10.26; N, 3.40; Br, 19.37. Found: C, 66.73; H, 10.11; N, 3.36; Br, 19.45.

N,N-di-n-pentyl-N-methyl-4-phenylbutylammonium bromide M.P. 61°–63° C.

Analysis calc. for $C_{21}H_{38}BrN$ Theory: C, 65.61; H, 9.96; N, 3.64; Br, 20.78. Found: C, 65.32; H, 9.87; N, 3.57; Br, 21.00.

N,N-dimethyl-N-isopropyl-4-phenylbutylammonium bromide M.P. 162°–164° C.

Analysis calc. for $C_{15}H_{26}BrN$ Theory: C, 60.00; H, 8.73; N, 4.66; Br, 26.61. Found: C, 59.85; H, 8.48; N, 4.54; Br, 26.71.

N,N-dimethyl-N-n-propyl-4-phenylbutylammonium bromide M.P. 93°–95° C.

Analysis calc. for $C_{15}H_{26}BrN$ Theory: C, 60.00; H, 8.73; N, 4.66; Br, 26.61. Found: C, 59.73; H, 8.45; N, 4.40; Br, 26.59.

N,N-dimethyl-N-n-pentyl-4-phenylbutylammonium bromide M.P. 76°–78° C.

Analysis calc. for $C_{17}H_{30}BrN$ Theory: C, 62.19; H, 9.21; N, 4.27; Br, 24.34. Found: C, 61.89; H, 9.02; N, 4.29; Br, 24.47.

N,N-dimethyl-N-n-hexyl-4-diphenylbutylammonium bromide M.P. 46°–48° C.

Analysis calc. for $C_{18}H_{32}BrN$ Theory: C, 63.15; H, 9.42; N, 4.09; Br, 23.34. Found: C, 62.92; H, 9.25; N, 4.17; Br, 23.52.

N,N-dimethyl-N-(1-methylpropyl)-4-phenylbutylammonium bromide M.P. 98°–100° C.

Analysis calc. for $C_{16}H_{28}BrN$ Theory: C, 61.14; H, 8.98; N, 4.46; Br, 25.42. Found: C, 60.92; H, 8.71; N, 4.46; Br, 25.58.

N,N-dimethyl-N-isobutyl-4-phenylbutylammonium bromide M.P. 113°–115° C.

Analysis calc. for $C_{16}H_{28}BrN$ Theory: C, 61.14; H, 8.98; N, 4.46; Br, 25.42. Found: C, 61.00; H, 8.86; N, 4.48; Br, 25.55.

N,N-di-n-propyl-N-methyl-4-phenylbutylammonium bromide M.P. 107°–109° C.

Analysis calc. for $C_{17}H_{30}BrN$ Theory: C, 62.19; H, 9.21; N, 4.27; Br, 24.34. Found: C, 62.10; H, 9.32; N, 4.06; Br, 24.53.

N,N-diethyl-N-methyl-4-phenylbutylammonium bromide M.P. 145°–147° C.

Analysis calc. for $C_{15}H_{26}BrN$ Theory: C, 60.00; H, 8.73; N, 4.66; Br, 26.61. Found: C, 60.27; H, 8.93; N, 4.84; Br, 26.90.

N,N-di-n-butyl-N-methyl-4-phenylbutylammonium bromide M.P. 70°–72° C.

Analysis calc. for $C_{19}H_{34}BrN$ Theory: C, 64.03; H, 9.62; N, 3.93; Br, 22.42. Found: C, 63.80; H, 9.37; N, 4.20; Br, 22.40.

N,N-dimethyl-N-n-butyl-4-phenylbutylammonium bromide M.P. 95°–96° C.

Analysis calc. for $C_{16}H_{28}BrN$ Theory: C, 61.14; H, 8.98; N, 4.46; Br, 25.42. Found: C, 60.94; H, 9.12; N, 4.60; Br, 25.63.

N,N-di-n-pentyl-N-ethyl-4-phenylbutylammonium bromide M.P. 41°–45° C.

Analysis calc. for $C_{22}N_{40}BrN$ Theory: C, 66.31; H, 10.12; N, 3.52; Br, 20.05. Found: C, 66.08; H, 9.88; N, 3.50; Br, 19.86.

N,N-dimethyl-N-ethyl-4-phenylbutylammonium bromide M.P. 160°–162° C.

Analysis calc. for $C_{14}H_{24}BrN$ Theory: C, 58.74; H, 8.45; N, 4.89; Br, 27.91. Found: C, 58.44; H, 8.22; N, 5.11; Br, 27.85.

N,N,N-triethyl-4-phenylbutylammonium bromide M.P. 58°–60° C.

Analysis calc. for $C_{16}H_{28}BrN$ Theory: C, 61.14; H, 8.98; N, 4.46; Br, 25.42. Found: C, 60.85; H, 8.70; N, 4.49; Br, 25.70.

N,N,N-tri-n-propyl-4-phenylbutylammonium bromide M.P. 113°–115° C.

Analysis calc. for $C_{19}H_{34}BrN$ Theory: C, 64.03; H, 9.62; N, 3.93; Br, 22.42. Found: C, 63.86; H, 9.54; N, 3.71; Br, 22.33.

N-methyl-N-(4-phenylbutyl)hexahydroazepinium bromide M.P. 129°–131° C.

Analysis calc. for $C_{17}H_{28}BrN$ Theory: C, 62.57; H, 8.65; N, 4.29; Br, 24.49. Found: C, 62.32; H, 8.43; N, 4.28; Br, 24.57.

N-methyl-N-(4-phenylbutyl)-tetrahydropyrrolium bromide M.P. 128°–130° C.

Analysis calc. for $C_{15}H_{24}BrN$ Theory: C, 60.40; H, 8.11; N, 4.70; Br, 26.79. Found: C, 60.47; H, 7.86; N, 4.86; Br, 26.63.

EXAMPLE 25

N,N,N-Trimethyl-4-phenylbutylammonium methanesulfate

A solution of 17 g. of N,N-dimethyl-4-phenylbutylamine in 500 ml. of diethyl ether was stirred at 0° C. in a flask equipped with a calcium sulfate drying tube while 9.1 ml. of dimethyl sulfate was added dropwise over ninety minutes. The reaction mixture then was warmed to room temperature and was stirred for twelve hours. The precipitate was collected by filtration and recrystallized from 300 ml. of acetone to afford 27.64 g. of N,N,N-trimethyl-4-phenylbutylammonium methanesulfonate. M.P. 122°–124° C.

Analysis calc. for $C_{14}H_{25}NSO_4$ Theory: C, 55.42; H, 8.31; N, 4.62; S, 10.60. Found: C, 55.62; H, 8.10; N, 4.68; S, 10.57.

EXAMPLE 26

Following the procedure set out in Example 25, N-(4-phenylbutyl)piperidine was reacted with dimethyl sulfate to afford N-methyl-N-(4-phenylbutyl)piperidinium methanesulfonate. M.P. 54°–56° C.

Analysis calc. for $C_{17}H_{29}NSO_4$ Theory: C, 59.45; H, 8.51; N, 4.08; S, 9.33. Found: C, 59.23; H, 8.64; N, 4.05; S, 9.12.

EXAMPLE 27

N-n-Heptyl-4-phenylbutylamine

A mixture of 125 g. of 4-phenylbutyl chloride and 250 g. of n-heptylamine was stirred and heated at 110° C. for four days. After cooling the reaction mixture to room temperature and adding 200 ml. of water, it was made alkaline by the addition of 5 N sodium hydroxide. The aqueous alkaline solution was extracted with diethyl ether. The ethereal extracts were combined and washed with water, and then the product was extracted into aqueous sulfuric acid solution. The acidic layer was separated, washed with fresh diethyl ether, and then made alkaline again by the addition of 5 N sodium hydroxide. The product was extracted from the aqueous alkaline solution into fresh diethyl ether. The ethereal extracts were combined, washed with water and dried. Removal of the solvent by evaporation under reduced pressure afforded 186 g. of the product as an oil. The oil was distilled to provide 135.46 g. of N-n-heptyl-4-phenylbutylamine. B.P. 160°–166° C. at 5 torr.

EXAMPLE 28

N-Acetyl-N-n-heptyl-4-phenylbutylamine

To a cold stirred solution of 25.67 g. of N-n-heptyl-4-phenylbutylamine in 70 ml. of acetone containing 22.1 g. of sodium carbonate and 70 ml. of water was added dropwise over sixty minutes a solution of 8.1 ml. of acetyl chloride in 140 ml. of acetone. During the addition the temperature of the reaction mixture was maintained below about 30° C. Upon completion of the addition, the reaction mixture was permitted to warm to 25° C. and then was stirred at that temperature for twelve hours.

The reaction mixture then was concentrated under reduced pressure to a volume of about 20 ml., and then diluted further with 60 ml. of fresh water. The aqueous solution was extracted several times with diethyl ether. The ethereal extracts were combined, washed with water, with 1 M citric acid solution, four additional times with water, and dried. Removal of the solvent by evaporation under reduced pressure provided 19.69 g. of N-acetyl-N-n-heptyl-4-phenylbutylamine.

EXAMPLE 29

N-Ethyl-N-n-heptyl-4-phenylbutylamine

To a stirred solution of 0.94 molar diborane in 220 ml of tetrahydrofuran (THF) was added dropwise over twenty minutes a solution of 19.69 g. of N-acetyl-N-n-heptyl-4-phenylbutylamine in 50 ml. of THF. The reaction mixture was then heated at reflux for twelve hours. After cooling the reaction mixture to room temperature, it was stirred while 75 ml. of cold (5° C.) 2 N hydrochloric acid was added dropwise over twenty minutes. The reaction mixture next was concentrated to a volume of about 80 ml. and then was diluted with 100 ml. of concentrated hydrochloric acid. The acid mixture was stirred and heated at reflux for one hour. The reaction mixture was cooled to room temperature and made alkaline by the addition of 5 N sodium hydroxide. The aqueous alkaline solution was extracted several times with diethyl ether. The ethereal extracts were combined, washed with water and extracted with 2 N sulfuric acid. The acidic extracts were combined and made alkaline by the addition of 5 N sodium hydroxide. The aqueous alkaline solution was extracted with diethyl ether, and the ethereal extracts were combined, washed with water, dried, and the solvent was removed therefrom by evaporation under reduced pressure to afford 15.22 g. of the product as an oil. The oil as formed was distilled to provide 13.8 g. of N-ethyl-N-n-heptyl-4-phenylbutylamine. B.P. 128°–129° C. at 0.1 torr.

EXAMPLE 30

Following the procedure set out in Examples 28-29, N-n-heptyl-N-n-pentanoyl-4-phenylbutylamine was prepared and reduced by reaction with diborane to provide N-n-pentyl-N-n-heptyl-4-phenylbutylamine.

EXAMPLE 31

N,N-Diethyl-N-n-heptyl-4-phenylbutylammonium bromide

In a flask equipped with a calcium sulfate drying tube, a solution of 4.33 g. of N-ethyl-N-n-heptyl-4-phenylbutylamine in 35 ml. of ethyl bromide was stirred and heated at reflux for forty-eight hours. The reaction mixture then was cooled to room temperature and the excess ethyl bromide was removed by evaporation under reduced pressure. The residue was dissolved in 50 ml. of ethyl acetate saturated with water, and the product precipitated therefrom upon cooling to 0° C. The precipitate was collected by filtration and recrystallized from fresh wet ethyl acetate to provide 5.5 g. of N,N-diethyl-N-n-heptyl-4-phenylbutylammonium bromide as a monohydrate. M.P. 48°-50° C.

Analysis calc. for $C_{21}H_{40}BrNO$ Theory: C, 62.67; H, 10.02; N, 3.48; Br, 19.85. Found: C, 62.72; H, 9.88; N, 3.32; Br, 19.65.

EXAMPLE 32

Following the procedure set forth in Example 31, N-n-pentyl-N-n-heptyl-4-phenylbutylamine prepared according to Example 30 was reacted with methyl bromide to provide N-n-heptyl-N-methyl-N-n-pentyl-4-phenylbutylammonium bromide. M.P. 55°-57° C.

Analysis calc. for $C_{23}H_{42}BrN$ Theory: C, 66.97; H, 10.26; N, 3.40; Br, 19.37. Found: C, 66.76; H, 10.04; N, 3.29; Br, 18.93.

EXAMPLE 33

N-n-Heptyl-4-(4-chlorophenyl)butyramide 4-(4-Chlorophenyl)-n-butyric acid was prepared by reacting 4-chlorobenzaldehyde with ethyl acetate and sodium cyanide to provide ethyl 4-(4-chlorophenyl)-4-oxo-butyrate, hydrolyzing the ethyl butyrate derivative to afford 4-(4-chlorophenyl)-4-oxobutyric acid, and then reducing the 4-oxo-group of said acid by reaction with zinc and hydrochloric acid.

To a stirred solution of 16.15 g. of 4-(4-chlorophenyl)-n-butyric acid in 200 ml. of benzene was added dropwise over thirty minutes 35 ml. of oxalyl chloride. Following complete addition, the reaction mixture was heated at reflux for three hours, and then cooled to room temperature. The unreacted oxalyl chloride was removed by evaporation under reduced pressure, and the remaining solution was diluted with 200 ml. of diethyl ether. The reaction mixture was cooled to 5° C. in an ice bath, and then 28.3 g. of n-heptyl amine in 30 ml. of diethyl ether was added dropwise over sixty minutes. The reaction mixture was stirred at 25° C. for twelve hours and then diluted with 100 ml. of water. The aqueous reaction mixture was extracted with diethyl ether, and the ethereal extract was washed with water, with 2 N hydrochloric acid, again with water, dried, and the solvent was removed therefrom by evaporation under reduced pressure to provide 24.45 g. of N-n-heptyl-4-(4-chlorophenyl)butyramide. M.P. 35°-38° C.

EXAMPLE 34

N-n-Heptyl-4-(4-chlorophenyl)butylamine

To a stirred solution of 268 ml. of 0.94 molar diborane in THF was added dropwise over ninety minutes a solution of 24.45 g. of N-n-heptyl-4-(4-chlorophenyl)-butyramide in 100 ml. of THF. The reaction mixture then was heated to reflux and stirred for twelve hours. After cooling the reaction mixture to 5° C. in an ice bath, excess 2 N hydrochloric acid was added to decompose any remaining diborane. The solvent next was removed by evaporation under reduced pressure, and the residue remaining was diluted with 100 ml. of conc. hydrochloric acid. The acidic reaction mixture was heated to reflux and stirred for forty-five minutes and then cooled again to room temperature. The acidic solution was made alkaline by the addition of 5 N sodium hydroxide solution, and the product was extracted from the alkaline solution into diethyl ether. The ethereal extracts were combined, washed with water and extracted into 2 N sulfuric acid. The aqueous acid solution was made alkaline by the addition of 5 N sodium hydroxide, and the alkaline solution was then extracted several times with diethyl ether. The ethereal extracts were combined, washed with water and dried. Evaporation of the solvent then afforded 21.86 g. of N-n-heptyl-4-(4-chlorophenyl)butylamine.

EXAMPLE 35

N-n-Heptyl-N-methyl-4-(4-chlorophenyl)butylamine

A solution of 10 g. of N-n-heptyl-4-(4-chlorophenyl)-butylamine, 9 ml. of ninety percent formic acid and 8.7 ml. of thirty-seven percent aqueous formaldehyde was heated at 100° C. until the evolution of carbon dioxide was observed. The reaction mixture was cooled and stored at room temperature for ten minutes. The reaction mixture was again heated to 100° C. and maintained at that temperature for twelve hours. After again cooling the mixture to room temperature, it was diluted with 40 ml. of 4 N hydrochloric acid, after which time the excess solvent was removed by evaporation under reduced pressure. The residual oil was diluted with water and then made alkaline by the addition of 5 N sodium hydroxide. The alkaline solution was extracted with diethyl ether. The ethereal extracts were combined and the product was extracted therefrom into 2 N sulfuric acid. The acidic extracts were combined and basified by the addition of 5 N sodium hydroxide. The alkaline solution was extracted with fresh diethyl ether, and the ethereal extracts were combined, washed with water and dried. Evaporation of the solvent provided 9.8 g. of N-n-heptyl-N-methyl-4-(4-chlorophenyl)-butylamine. The amine so formed was dissolved in 25 ml. of ethyl acetate and added in one portion to a solution of 3.0 g. of oxalic acid in 150 ml. of ethyl acetate. The precipitate which formed was collected by filtration and air dried to provide 12.13 g. of N-n-heptyl-N-methyl-4-(4-chlorophenyl)butylammonium oxalate. M.P. 102°-104° C.

Analysis calc. for $C_{20}H_{32}ClNO_4$ Theory: C, 62.24; H, 8.36; N, 3.63; Cl, 9.19. Found: C, 62.28; H, 8.45; N, 3.46; Cl, 9.20.

EXAMPLE 36

N,N-Dimethyl-N-n-heptyl-4-(4-chlorophenyl)-butylammonium bromide

A solution of 5.0 g. of N-n-heptyl-N-methyl-4-(4-chlorophenyl)butylamine in 100 ml. of diethyl ether was stirred at 25° C. while methyl bromide gas was bubbled into the solution until saturation was reached. The reaction mixture was stirred at 25° C. for eighteen hours and then cooled to 0° C., whereupon a solid precipitate formed. The precipitate was stored at room temperature for forty-eight hours, and then was collected by filtration and recrystallized from 50 ml. of ethyl acetate to provide 5.55 g. of N,N-dimethyl-N-n-heptyl-4-(4-chlorophenyl)butylammonium bromide. M.P. 58°-60° C.

Analysis calc. for $C_{19}H_{33}BrClN$ Theory: C, 58.39; H, 8.51; N, 3.58; Cl, 9.07; Br, 20.44. Found: C, 58.16; H, 8.27; N, 3.58; Cl, 9.34; Br, 20.58.

EXAMPLE 37

N,N-Diethyl-N-n-heptyl-4-(4-chlorophenyl)butylammonium bromide

A solution of 1.27 g. of N-ethyl-N-n-heptyl-4-(4-chlorophenyl)butylamine and 20 ml. of ethyl bromide was heated at reflux and stirred for one week. The reaction mixture then was cooled, and excess ethyl bromide was removed by evaporation under reduced pressure to leave the product as an oil. The oil was crystallized from ethyl acetate which was saturated with water to afford 1.47 g. of N,N-diethyl-N-n-heptyl-4-(4-chlorophenyl)butylammonium bromide as a dihydrate. M.P. 29°-30° C.

Analysis calc. for $C_{21}H_{41}BrClNO$ Theory: C, 55.45; H, 9,08; N, 3.08; Cl, 7.79; Br, 17.56. Found: C, 55.15; H, 8.87; N, 3.03; Cl, 8.08; Br, 17.57.

EXAMPLE 38

N,N,N-Triethyl-4-(4-chlorophenyl)butylammonium bromide

A solution of 4.3 g. of N,N-diethyl-4-(4-chlorophenyl)butylamine and 35 ml. of ethyl bromide was heated at reflux and stirred for three days. The reaction mixture was cooled to room temperature and concentrated to an oil by evaporation of excess ethyl bromide under reduced pressure. The oil so formed was crystallized from methyl ethyl ketone to provide 4.99 g. of N,N,N-triethyl-4-(4-chlorophenyl)butylammonium bromide M.P. 106°-108° C.

Analysis calc. for $C_{16}H_{27}BrClN$ Theory: C, 55.10; H, 7.80; N, 4.02; Br, 22.91; Cl, 10.17. Found: C, 55.12; H, 7.83; N, 4.23; Br, 23.07; Cl, 10.23.

EXAMPLE 39

N,N-Di-n-pentyl-N-methyl-4-(4-chlorophenyl)-butylammonium bromide

Methyl bromide gas was bubbled into a solution of 5.0 g. of N,N-di-n-pentyl-4-(4-chlorophenyl)butylamine in 150 ml. of diethyl ether until the solution was saturated. The reaction mixture was stored at room temperature for two days, and then the precipitate which had formed was collected by filtration. The precipitate was recrystallized from 50 ml. of ethyl acetate to afford 5.4 g. of N,N-di-n-pentyl-N-methyl-4-(4-chlorophenyl)-butylammonium bromide. M.P. 81°-83° C.

Analysis calc. for $C_{21}H_{37}BrClN$ Theory: C, 60.21; H, 8.90; N, 3.34; Br, 19.08; Cl, 8.46. Found: C, 60.22; H, 8.64; N, 3.22; Br, 19.30; Cl, 8.90.

EXAMPLE 40

N-n-Heptyl-1-methyl-4-phenylbutylamine

A solution of 10 g. of methyl 3-phenylpropyl ketone and 7.1 g. of n-heptyl amine in 80 ml. of 2B ethanol containing 2 g. of 5 percent palladium on carbon was stirred for twelve hours at 50° C. under a hydrogen gas atmosphere of 50 p.s.i. The reaction mixture then was cooled to room temperature and the solvent was removed by evaporation under reduced pressure to provide an oil. The oil next was dissolved in 100 ml. of diethyl ether, and the ethereal solution was washed with 5 N sodium hydroxide and with water. After drying the solution, the solvent was evaporated to afford 12.34 g. of N-n-heptyl-1-methyl-4-phenylbutylamine.

EXAMPLE 41

N-n-Heptyl-N-methyl-1-methyl-4-phenylbutylamine

A solution of 12.34 g. of N-n-heptyl-1-methyl-4-phenylbutylamine, 12.2 ml. of ninety percent formic acid and 11.6 ml. of thirty-seven percent aqueous formaldehyde was heated at 100° C. for twelve hours and then cooled to room temperature. The reaction mixture was acidfied with 40 ml. of 4 N hydrochloric acid, and then was concentrated to a volume of about 20 ml. by evaporation under reduced pressure. The acidic mixture next was made alkaline with 5 N sodium hydroxide, and the alkaline solution was extracted several times with diethyl ether. The ethereal extracts were combined, washed with water, dried, and the solvent was removed by evaporation to provide 12.49 g. of the product as a crude oil. The oil was distilled to afford 10.7 g. of N-n-heptyl-N-methyl-1-methyl-4-phenylbutylamine. B.P. 120°-124° C. at 0.5 torr.

EXAMPLE 42

N,N-Dimethyl-N-n-heptyl-1-methyl-4-phenylbutylammonium bromide

Into a stirred solution of 5.0 g. of N-n-heptyl-N-methyl-1-methyl-4-phenylbutylamine in 150 ml. of diethyl ether was bubbled methyl bromide gas until the solution was saturated. The reaction mixture then was stirred for four days, during which time a white precipitate formed. The precipitate was collected by filtration and was recrystallized from 50 ml. of ethyl acetate to provide 5.215 g. of N,N-dimethyl-N-n-heptyl-1-methyl-4-phenylbutylammonium bromide. M.P. 70°-72° C.

Analysis calc. for $C_{20}H_{36}BrN$ Theory: C, 64.85; H, 9.80; N, 3.78; Br, 21.57. Found: C, 65.12; H, 9.51; N, 3.91; Br, 21.64.

EXAMPLE 43

N,N,N-Triethyl-1-methyl-4-phenylbutylammonium bromide

A solution of 3.65 g. of N,N-diethyl-(1-methyl-4-phenyl)butylamine in 35 ml. of ethyl bromide was heated at reflux and stirred for seven days. After cooling the reaction mixture to room temperature and adding 50 ml. of diethyl ether, the white precipitate which formed was filtered off. Recrystallization of the precipitate from 50 ml. of methyl ethyl ketone afforded 619 mg. of N,N,N-triethyl-1-methyl-4-phenylbutylammonium bromide. M.P. 123°-125° C.

Analysis calc. for $C_{17}H_{30}BrN$ Theory: C, 62.19; H, 9.21; N, 4.27; Br, 24.34. Found: C, 62.13; H, 9.06; N, 4.29; Br, 24.05.

EXAMPLE 44

1-Methyl-4-(4-chlorophenyl)butylamine

A solution of 19.07 g. of methyl 3-(4-chlorophenyl)-propyl ketone, 17.6 ml. of formamide and 14.7 ml. of ninety-seven percent aqueous formic acid was heated at 160° C. and stirred for twelve hours. After cooling the reaction mixture to room temperature, it was diluted with 100 ml. of water, and the product was extracted therefrom into diethyl ether. The ethereal extracts were combined, washed with water and dried. Evaporation of the solvent afforded 20.7 g. of an oil which was dissolved in 84 ml. of conc. hydrochloric acid and 400 ml. of twenty-five percent dioxane in water, and the aqueous solution was heated at reflux for twelve hours. After cooling the reaction mixture to 30° C., it was made alkaline with 5 N sodium hydroxide. The aqueous alkaline solution was extracted several times with diethyl ether. The ethereal extracts were combined, washed with water, dried and the solvent was evaporated therefrom to afford 15.26 g. of 1-methyl-4-(4-chlorophenyl)butylamine.

EXAMPLE 45

N,N-Dimethyl-1-methyl-4-(4-chlorophenyl)butylamine 7.6 Grams of 1-methyl-4-(4-chlorophenyl)butylamine was reacted with 9.9 ml. of ninety percent formic acid and 9.5 ml. of thirty-seven percent aqueous formaldehyde to provide 7.05 g. of N,N-dimethyl-1-methyl-4-(4-chlorophenyl)butylamine. The free amine was reacted with hydrogen chloride to form N,N-dimethyl-1-methyl-4-(4-chlorophenyl)butylaminium chloride. M.P. 109°–111° C.

Analysis calc. for $C_{13}H_{21}Cl_2N$ Theory: C, 59.55; H, 8.07; N, 5.34; Cl, 27.04. Found: C, 59.51; H, 7.88; N, 5.17; Cl, 27.39.

EXAMPLE 46

N,N,N-Trimethyl-[1-methyl-4-(4-chlorophenyl)butyl]ammonium bromide

A solution of 3.02 g. of N,N-dimethyl-1-methyl-4-(4-chlorophenyl)butylamine in 150 ml. of diethyl ether was stirred at 25° C. while methyl bromide was bubbled into the solution until it was saturated. The reaction mixture then was stirred for twenty-four hours and the precipitate which had formed was then collected by filtration. The precipitate was recrystallized from 50 ml. of isopropyl alcohol to provide 2.6 g. of N,N,N-trimethyl-[1-methyl-4-(4-chlorophenyl)butyl]ammonium bromide. M.P. 204°–206° C. (dec.)

Analysis calc. for $C_{14}H_{23}BrClN$ Theory: C, 52.43; H, 7.23; N, 4.37; Br, 24.92; Cl, 11.05. Found: C, 52.54; H, 7.02; N, 4.21; Br, 24.77; Cl, 11.16.

EXAMPLE 47

N,N-Diethyl-N-n-heptyl-4-(4-nitrophenyl)-butylammonium bromide

A solution of 3.0 g. of N-ethyl-N-n-heptyl-4-(4-nitrophenyl)butylamine dissolved in 20 ml. of ethyl bromide was stirred and heated at reflux for four and one-half days. The reaction mixture was cooled to 25° C. and stored at that temperature for seventy-two hours. The excess ethyl bromide was removed by evaporation under reduced pressure, thus providing the product as an oil. The oil so formed was crystallized from ethyl acetate and acetone and then recrystallized from ethyl acetate and acetone to afford 2.06 g. of N,N-diethyl-N-n-heptyl-4-(4-nitrophenyl)butylammonium bromide. M.P. 67°–69° C.

Analysis calc. for $C_{21}H_{37}BrN_2O_2$ Theory: C, 58.73; H, 8.68; N, 6.52; Br, 18.61; Found: C, 58.49; H, 8.55; N, 6.55; Br, 18.56.

EXAMPLE 48

4-(4-Methoxyphenyl)butylamine

Ethyl 4-methoxycinnamate was hydrogenated to afford ethyl 3-(4-methoxyphenyl)propionate. The latter compound was reduced by reaction with lithium aluminum hydride to provide 3-(4-methoxyphenyl)propanol. The propanol was reacted with methanesulfonyl chloride to give 3-(4-methoxyphenyl)propyl methyl sulfonate, which was then reacted with sodium cyanide to provide 4-(4-methoxyphenyl)butyronitrile.

Analysis calc. for $C_{11}H_{13}NO$. Theory: C, 75.40; H, 7.48; N, 7.99. Found: C, 75.24; H, 7.21; N, 7.90.

Reduction of the butyronitrile by reaction with diborane gave 4-(4-methoxyphenyl)butylamine.

EXAMPLE 49

N,N-Dimethyl-4-(4-methoxyphenyl)butylamine

To a cold stirred solution of 43.5 ml. of ninety percent formic acid was added slowly 30.35 g. of 4-(4-methoxyphenyl)butylamine and 41.5 ml. of thirty-seven percent aqueous formaldehyde. The reaction mixture was heated at 100° C. until carbon dioxide started evolving, and then the mixture was cooled to room temperature and stored for fifteen minutes. The mixture then again was heated at 100° C. and stirred for twelve hours. After cooling the reaction mixture to 30° C., it was acidified by the addition of 80 ml. of 4 N hydrochloric acid. The mixture was concentrated by evaporation and diluted with water. The aqueous acidic solution was washed with diethyl ether and then made alkaline by the addition of 5 N sodium hydroxide. The product was extracted from the alkaline solution into fresh diethyl ether, and the ethereal extracts were combined, washed with water and dried. Removal of the solvent by evaporation under reduced pressure provided 26.67 g. of N,N-dimethyl-4-(4-methoxyphenyl)butylamine. B.P. 124°–125° C. at 5 torr. The amine was further purified by reaction with hydrogen chloride to give the hydrochloride salt, which then was recrystallized from 500 ml. of 95 percent ethyl acetate in methanol. M.P. 127°–129° C.

Analysis calc. for $C_{13}H_{22}ClNO$ Theory: C, 64.05; H, 9.10; N, 5.75; Cl, 14.54. Found: C, 63.88; H, 8.88; N, 5.77; Cl, 14.73.

EXAMPLE 50

N,N,N-Trimethyl-4-(4-methoxyphenyl)butylammonium bromide

N,N-Dimethyl-4-(4-methoxyphenyl)butylamine (4.35 g.) was reacted with methyl bromide according to the procedure of Example 46 to provide 4.95 g. of N,N,N-trimethyl-4-(4-methoxyphenyl)butylammonium bromide, which was recrystallized from acetone and methanol. M.P. 166°–168° C.

Analysis calc. for $C_{14}H_{24}BrNO$ Theory: C, 55.63; H, 8.00; N, 4.63; Br, 26.44. Found: C, 55.94; H, 7.73; N, 4.72; Br, 26.73.

EXAMPLE 51

N,N-Dimethyl-3-(4-chlorophenyl)propionamide

A solution of 18.4 g. of 3-(4-chlorophenyl)propionic acid and 42.5 ml. of oxalyl chloride in 200 ml. of benzene was stirred and heated at reflux for three hours. The solution then was cooled to room temperature and concentrated to an oil by evaporation under reduced pressure. The acid chloride so formed was dissolved in 250 ml. of diethyl ether, cooled to 5° C., and stirred while gaseous dimethylamine was bubbled through the solution. After the reaction mixture was saturated with dimethylamine, it was stirred at 25° C. for one hour and then washed with water and with 2 N hydrochloric acid and dried. Evaporation of the solvent provided 21.9 g. of N,N-dimethyl-3-(4-chlorophenyl)propionamide.

EXAMPLE 52

N,N-Dimethyl-N-n-pentyl-3-(4-chlorophenyl)-propylammonium bromide

Reaction of 21.9 g. of N,N-dimethyl-3-(4-chlorophenyl)propionamide with diborane provided 16.88 g. of N,N-dimethyl-3-(4-chlorophenyl)propylamine. B.P. 147–148 at 30 torr. A solution of 5.71 g. of the free amine in 150 ml. of diethyl ether was stirred at room temperature while 3.0 g. of n-pentyl bromide was added in one portion. The reaction mixture then was stirred at room temperature for twelve hours, during which time a white precipitate formed. The precipitate was collected by filtration and recrystallized from 125 ml. of methyl ethyl ketone and 10 ml. of methanol to provide N,N-dimethyl-N-n-pentyl-3-(4-chlorophenyl)-propylammonium bromide.

EXAMPLE 53

N,N-Dimethyl-4-(4-fluorophenyl)butylamine

Reduction of cyclopropyl 4-fluorophenyl ketone by reaction with sodium borohydride gave cyclopropyl-4-fluorophenylcarbinol. Reaction of the cyclopropyl carbinol with hydrogen chloride in acetic acid effected opening of the cyclopropyl ring, chlorination and dehydration to afford 1-chloro-4-(4-fluorophenyl)-3-butene. The chlorobutene was reacted with dimethylamine in ethanol at 100° C. for forty-eight hours to provide N,N-dimethyl-4-(4-fluorophenyl)-3-butenylamine. A solution of 54.4 g. of the butenylamine in 343 ml. of ethanol containing 2.5 g. of Raney Nickel was hydrogenated to provide 47.71 g. of N,N-dimethyl-4-(4-fluorophenyl)-butylamine. B.P. 115°–118° C. at 12 torr.

EXAMPLE 54

Following the procedure set out in Example 46, 8.77 g. of N,N-dimethyl-4-(4-fluorophenyl)butylamine was reacted with methylbromide to provide a white solid which was crystallized from acetone and methanol to afford 9.7 g. of N,N,N-trimethyl-4-(4-fluorophenyl)-butylammonium bromide. M.P. 160°–162° C.

Analysis calc. for $C_{13}H_{21}BrFN$ Theory: C, 53.80; H, 7.29; N, 4.83; Br, 27.53. Found: C, 54.09; H, 7.24; N, 4.78; Br, 27.76.

EXAMPLES 55–57

By following the procedures set out in Examples 53 and 54, the following salts were prepared by starting with the appropriate cyclopropyl phenyl ketone.

N,N,N-Trimethyl-4-(4-ethylphenyl)butylammonium bromide M.P. 147°–149° C.

Analysis calc. for $C_{15}H_{26}BrN$ Theory: C, 60.00; H, 8.73; N, 4.66; Br, 26.61. Found: C, 59.76; H, 8.48; N, 4.65; Br, 26.66.

N,N,N-Trimethyl-4-(4-chlorophenyl)butylammonium bromide M.P. 211°–213° C.

Analysis calc. for $C_{13}H_{21}BrClN$ Theory: C, 50.91; H, 6.90; N, 4.57; Br, 26.05; Cl, 11.56. Found: C, 50.86; H, 6.75; N, 4.52; Br, 26.11; Cl, 11.21.

N,N,N-Trimethyl-4-(4-bromophenyl)butylammonium bromide M.P. 226°–228° C.

Analysis calc. for $C_{13}H_{21}Br_2N$ Theory: C, 44.47; H, 6.03; N, 3.99; Br, 45.51. Found: C, 44.65; H, 6.08; N, 4.21; Br, 45.86.

EXAMPLE 58

3-Phenylpropyl n-propyl ketone

Propyl magnesium bromide was prepared by reacting 24 g. of magnesium with 128 g. of propyl bromide in 450 ml. of diethyl ether. To the stirred Grignard reagent thus prepared was added dropwise a solution of 100 g. of 4-phenylbutylnitrile in 70 ml. of diethyl ether. Following complete addition, the reaction mixture was heated at reflux for one hour, and then cooled to room temperature and stirred for an additional twelve hours. The reaction mixture was then poured slowly into 100 g. of ice and 250 ml. of conc. hydrochloric acid. The organic layer was separated, washed with water and dried. Evaporation of the solvent and distillation of the product provided 57.9 g. of 3-phenylpropyl n-propyl ketone. B.P. 134°–137° C. at 10 torr.

EXAMPLE 59

1-n-Propyl-4-phenylbutylamine

A solution of 57.9 g. of 3-phenylpropyl n-propyl ketone, 46 ml. of ninety-seven percent formic acid and 55 ml. of formamide was stirred and heated at 160° C. for twelve hours. The reaction mixture then was cooled to room temperature and diluted with 100 ml. of water. The aqueous mixture was extracted three times with 100 ml. portions of diethyl ether, and the ethereal extracts were combined, washed with water and dried. Removal of the solvent by evaporation under reduced pressure afforded 63.2 g. of N-formyl-1n-propyl-4-phenylbutylamine. The N-formyl amine thus formed was dissolved in 1000 ml. of a 25 percent solution of dioxane in water containing 168 ml. of conc. hydrochloric acid. The acidic solution was stirred and heated at reflux for twelve hours. The mixture next was cooled to room temperature, extracted with diethyl ether, and then made alkaline by the addition of 5 N sodium hydroxide. The alkaline solution was extracted with diethyl ether, and the ethereal extracts were combined, washed with water and dried. Evaporation of the solvent therefrom afforded 51 g. of 1-n-propyl-4-phenylbutylamine.

EXAMPLE 60

Following the procedure set out in Example 49, 38.2 g. of 1-n-propyl-4-phenylbutylamine was reacted with 51.5 ml. of ninety percent formic acid and 40 ml. of thirty-seven percent aqueous formaldehyde to provide, after distillation, 37.1 g. of N,N-dimethyl-1-n-propyl-4-phenylbutylamine. B.P. 118°–120° C. at 5 torr.

EXAMPLE 61

N,N,N-Trimethyl-1-n-propyl-4-phenylbutylammonium bromide

A solution of 9.0 g. of N,N-dimethyl-1-n-propyl-4-phenylbutylamine in 150 ml. of diethyl ether saturated with methyl bromide gas was stirred at 25° C. for forty-eight hours. The precipitated product was collected by filtration and recrystallized from 250 ml. of acetone to provide 9.74 g. of N,N,N-trimethyl-1-n-propyl-4-phenylbutylammonium bromide. M.P. 158°–160° C.

Analysis calc. for $C_{16}H_{28}BrN$ Theory: C, 61.14; H, 8.98; N, 4.46; Br, 25.42. Found: C, 61.08; H, 8.90; N, 4.28; Br, 25.54.

EXAMPLE 62

N,N,N-Trimethyl-1-ethyl-4-phenylbutylammonium bromide

Ethyl magnesium bromide was reacted with 4-phenylbutylnitrile to provide ethyl 3-phenylpropyl ketone. The ketone was reacted with formamide and formic acid to afford 1-ethyl-4-phenylbutylamine. Methylation of the amine by reaction with formaldehyde and formic acid provided N,N-dimethyl-1-ethyl-4-phenylbutylamine. Quaternization of 6.2 g. of the dimethylamine according to the procedure of Example 62 afforded 6.56 g. of N,N,N-Trimethyl-1-ethyl-4-phenylbutylammonium bromide. M.P. 183°–185° C.

Analysis calc. for $C_{15}H_{26}BrN$ Theory: C, 60.00; H, 8.73; N, 4.66; Br, 26.61. Found: C, 60.02; H, 8.68; N, 4.66; Br, 26.79.

EXAMPLE 63

1,1-Dimethyl-4-phenylbutylamine

Isobutylnitrile was reacted with 3-phenylpropyl bromide in the presence of lithium diisopropylamide to provide 2,2-dimethyl-5-phenylpentylnitrile. Hydrolysis of the nitrile by reaction with potassium hydroxide in ethylene glycol afforded 2,2-dimethyl-5-phenyl-pentanoic acid. To a cold stirred solution of 20.6 g. of the pentanoic acid and 11.1 g. of triethylamine in 75 ml. of acetone was added dropwise over thirty minutes 11.9 g. of cold (0° to −5° C.) ethyl chloroformate. After the addition was complete, the reaction mixture was stirred for twenty minutes at 0° C., and then a solution of 13 g. of sodium azide in 33 ml. of water was added dropwise over twenty-five minutes. The aqueous reaction mixture was stirred for an additional thirty minutes at 0° C., and then diluted with an additional 150 ml. of water. The aqueous solution was extracted four times with 130 ml. portions of toluene. The toluene extracts were combined, washed with water, dried, and then heated at 100° C. for one hour. Removal of the solvent by evaporation under reduced pressure then provided a residue which next was dissolved in 150 ml. of 8 N hydrochloric acid. The acidic solution was stirred and heated for twenty minutes at 100° C., and then was heated at reflux for an additional twenty minutes. After cooling the reaction mixture to room temperature, it was diluted with water, washed with diethyl ether, and then made alkaline by the addition of 5 N sodium hydroxide. The alkaline solution was extracted with diethyl ether. The ethereal extracts were combined, washed with water and dried. Evaporation of the solvent gave 17.2 g. of 1,1-dimethyl-4-phenylbutylamine.

EXAMPLE 64

N,N,N-Trimethyl-1,1-dimethyl-4-phenylbutylammonium bromide

Reaction of 17.2 g. of 1,1-dimethyl-4-phenylbutylamine with 22.3 ml. of ninety percent formic acid and 23.6 ml. of thirty-seven percent formaldehyde afforded, after work-up of the reaction mixture and distillation of the product, 17.1 g. of N,N-dimethyl-1,1-dimethyl-4-phenylbutylamine. B.P. 109°–112° C. at 5 torr.

A solution of 8.5 g. of the dimethylamine derivative in 100 ml. of diethyl ether saturated with methyl bromide was stirred at 25° C. for two months and then filtered. The precipitate was recrystallized from 140 ml. of acetone and 10 ml. of methanol to provide 8.3 g. of N,N,N-trimethyl-1,1-dimethyl-4-phenylbutylammonium bromide. M.P. 194°–196° C.

Analysis calc. for $C_{15}H_{26}BrN$ Theory: C, 60.00; H, 8.73; N, 4.66; Br, 26.61. Found: C, 59.74; H, 8.77; N, 4.56; Br, 26.33.

EXAMPLE 65

N,N,N-Trimethyl-4-(4-ethoxyphenyl)butylammonium bromide

A solution of 210 g. of 4-ethoxy cinnamic acid in 1775 ml. of tetrahydrofuran was hydrogenated at 25° C. in the presence of 15 g. of five percent palladium on carbon to provide 100 g. of 3-(4-ethoxyphenyl)propionic acid. M.P. 93°–95° C. The acid so formed was reduced by reaction with 30.6 g. of lithium aluminum hydride to provide 101 g. of 3-(4-ethoxyphenyl)propanol. The alcohol so formed then was reacted with 52 ml. of methanesulfonyl chloride to give 156 g. of 3-(4-ethoxyphenyl)propyl methyl sulfonate, which when reacted with 43 g. of sodium cyanide gave 45.9 g. of 4-(4-ethoxyphenyl)butylnitrile. The nitrile was reduced by reaction with diborane to provide 4-(4-ethoxyphenyl)butylamine.

A solution of 15.82 g. of 4-(4-ethoxyphenyl)butylamine, 19 g. of ninety percent formic acid and 7.45 g. of thirty-seven percent aqueous formaldehyde was stirred and heated at 100° C. for twelve hours. The reaction mixture then was cooled to 25° C. and diluted with 100 ml. of water. The aqueous reaction mixture was made acidic by the addition of 4 N hydrochloric acid, and the acidic solution was concentrated in volume by evaporation and then diluted with water. The acidic solution next was made alkaline by the addition of 5 N sodium hydroxide, and the aqueous alkaline solution was extracted several times with diethyl ether. The ethereal extracts were combined, washed with water and dried, and the solvent was evaporated therefrom to provide 15.9 g. of the product as an oil. The oil was distilled to afford 8.86 g. of N,N-dimethyl-4-(4-ethoxyphenyl)butylamine. B.P. 142°–145° C. at 7 torr.

A solution of 2.9 g. of N,N-dimethyl-4-(4-ethoxyphenyl)butylamine in 150 ml. of diethyl ether saturated with methyl bromide was stirred at 25° C. for seventy-two hours. The precipitate which had formed was collected by filtration and was recrystallized from 200 ml. of methyl ethyl ketone to provide 3.27 g. of N,N,N-trimethyl-4-(4-ethoxyphenyl)butylammonium bromide. M.P. 151°–153° C.

Analysis calc. for $C_{15}H_{26}BrNO$ Theory: C, 56.96; H, 8.29; N, 4.43; Br, 25.26. Found: C, 56.78; H, 7.99; N, 4.48; Br, 25.24.

EXAMPLES 66–67

Following the procedure set out in Example 65, the following quaternary ammonium salts were prepared from the appropriate cinnamic acid.

N,N,N-Trimethyl-4-(3-chlorophenyl)butylammonium bromide M.P. 135°–137° C.

Analysis calc. for $C_{13}H_{21}BrClN$ Theory: C, 50.91; H, 6.90; N, 4.57; Br, 26.05; Cl, 11.56. Found: C, 51.14; H, 6.74; N, 4.73; Br, 26.22; Cl, 11.36.

N,N,N-Trimethyl-4-(4-methylphenyl)butylammonium bromide M.P. 156°–158° C.

Analysis calc. for $C_{14}H_{24}BrN$ Theory: C, 58.74; H, 8.45; N, 4.89; Br, 27.91. Found: C, 58.64; H, 8.66; N, 4.96; Br, 28.18.

EXAMPLE 68 dl-N,N,N-Trimethyl-1-methyl-4-phenylbutylammonium bromide

A solution of 5.15 g. of dl-N,N-dimethyl-1-methyl-4-phenylbutylamine in 75 ml. of diethyl ether saturated with methyl bromide was stirred at 25° C. for twelve hours. The precipitate which had formed was collected by filtration and recrystallized from acetone and methanol to afford 7.05 g. of dl-N,N,N-trimethyl-1-methyl-4-phenylbutylammonium bromide. M.P. 197°–199° C.

Analysis calc. for $C_{14}H_{24}BrN$ Theory: C, 58.74; H, 8.45; N, 4.89; Br, 27.91. Found: C, 59.02; H, 8.30; N, 5.13; Br, 28.03.

EXAMPLE 69 d(+)-N,N,N-Trimethyl-1-methyl-4-phenylbutylammonium bromide

Sixty-three grams of methyl 3-phenylpropyl ketone was reacted with 59.5 g. of d(+)-α-methyl benzylamine to afford 115 g. of d(+)-N-(α-methylbenzyl)-1-methyl-4-phenylbutylimine. The imine so produced was reduced by hydrogenation in the presence of Raney Nickel to afford diastereomeric N-(α-methylbenzyl)-1-methyl-4-phenylbutylamine, which was purified by distillation. The amine was reacted with hydrochloric acid to afford the hydrochloride salt, which upon successive crystallizations from ethyl acetate and methanol provided 33.79 g. of d(+)-N-(α-methylbenzyl)-1-methyl-4-phenylbutylaminium chloride. M.P. 156°–158° C. $\alpha_D^{25°}$ ($CH_3OH$)+46.4°.

Hydrogenation of 9.12 g. of d(+)-N-(α-methylbenzyl)-1-methyl-4-phenylbutylamine in the presence of five percent palladium on carbon effected debenzylation to afford d(+)-1-methyl-4-phenylbutylamine. The amine so formed was then hydrogenated at 50° C. for twelve hours in the presence of 25 ml. of thirty-seven percent aqueous formaldehyde to provide d(+)-N,N-dimethyl-1-methyl-4-phenylbutylamine. The amine was converted to a hydrochloride salt by reaction with hydrogen chloride, and the salt was recrystallized from ethyl acetate and methanol. M.P. 123°–125° C. $[\alpha]_D^{25°}$ ($CH_3OH$)+12.4°.

Analysis calc. for $C_{13}H_{22}ClN$ Theory: C, 68.55; H, 9.74; N, 6.15; Cl, 15.56. Found: C, 68.60; H, 9.61; N, 6.15; Cl, 15.55.

The hydrochloride salt next was dissolved in 50 ml. of water and the aqueous solution was made alkaline with 5 N sodium hydroxide. The aqueous alkaline solution was extracted with diethyl ether, and the ethereal extract was washed with water, dried, and the solvent removed by evaporation to provide d(+)-N,N-dimethyl-1-methyl-4-phenylbutylamine. A solution of 2.07 g. of the amine in 150 ml. of diethyl ether was stirred and saturated with methyl bromide. The ethereal solution was stored at 25° C. for forty-eight hours, and the precipitate which had formed was collected by filtration and recrystallized from 40 ml. of isopropyl alcohol, affording 2.23 g. of d(+)-N,N,N-trimethyl-1-methyl-4-phenylbutylammonium bromide. M.P. 206°–208° C. $[\alpha]_D^{25°}$ ($CH_3OH$)+24.9°.

Analysis calc. for $C_{14}H_{24}BrN$ Theory: C, 58.74; H, 8.45; N, 4.89; Br, 27.91. Found: C, 58.68; H, 8.37; N, 4.63; Br, 27.80.

EXAMPLE 70

Following the procedure set out in Example 71, 1(−)-1-methyl-4-phenylbutylamine was isolated and dimethylated to provide 1-N,N-dimethyl-1-methyl-4-phenylbutylamine, which then was quaternized by reaction with methyl bromide to give 1(−)N,N,N-trimethyl-1-methyl-4-phenylbutylammonium bromide. M.P. 210°–212° C. $[\alpha]_D^{25°}$ ($CH_3OH$)−24.9°

Analysis calc. for $C_{14}H_{24}BrN$ Theory: C, 58.74; H, 8.45; N, 4.89; Br, 27.91. Found: C, 58.47; H, 8.27; N, 4.62; Br, 27.79.

EXAMPLE 71

N,N-Dimethyl-N-n-heptyl-3-phenylpropylammonium p-toluenesulfonate 1.69 Grams of N-methyl-N-n-heptyl-3-phenylpropylammonium oxalate was converted to 1.29 g. of its free base with sodium hydroxide in diethyl ether. The 1.29 g. of N-methyl-N-n-heptyl-3-phenylpropylamine was placed in a 50 ml. round bottom flask. 1.08 Grams of methyl p-toluenesulfonate in 10 ml. methyl ethyl ketone was added. The mixture was refluxed for 2 hours and then cooled. Thin layer chromatography indicated no secondary amine was left. The methyl ethyl ketone was evaporated in vacuo, leaving an oily substance. Crystallization from ethyl acetate yielded 1.63 g. N,N-dimethyl-N-n-heptyl-3-phenylpropylammonium p-toluenesulfonate. M.P. 91°–93° C.

Analysis calc. for $C_{25}H_{39}NO_3S$ Theory: C, 69.24; H, 9.07; N, 3.23; S, 7.39. Found: C, 69.10; H, 8.84; N, 3.40; S, 7.55.

EXAMPLE 72

N,N,N-Trimethyl-4(4-nitrophenyl)butylammonium bromide 5.14 Grams of N,N-dimethyl-4(4-nitrophenyl)butylamine was placed in 150 ml. diethyl ether in a 300 ml. round flask. Methyl bromide was bubbled through the mixture until it was saturated. A precipitate appeared after 10 minutes. The mixture was stirred at room temperature for 4 days. The solids were filtered off and recrystallized from 75 ml. isopropanol to yield 6.77 g. A second recrystallization in 100 ml. of isopropanol yielded 6.44 g. of N,N,N-trimethyl-4[4-nitrophenyl]butylammonium bromide. M.P. 182°–184° C.

Analysis calc. for $C_{13}H_{21}BrN_2O_2$. Theory: C, 49.22; H, 6.67; N, 8.83. Found: C, 49.33; H, 6.51; N, 8.76.

EXAMPLE 73

N,N-Diethyl-N-n-heptyl-4(4-methoxyphenyl)butylammonium p-toluenesulfonate

24 Grams of N-ethyl-N-n-heptyl-4-(4-methoxyphenyl) butylamine was placed in a 500 ml. round bottom flask and 200 ml. ethyl bromide was added. The mixture was refluxed for 3½ days. Thin layer chromatography indicated very little secondary amine left. The excess ethyl bromide was evaporated in vacuo leaving an oil, N,N-diethyl-N-n-heptyl-4(4-methoxyphenyl)butylammonium bromide which next was converted to the hydroxide form as follows: Using 350 ml. BIO-RAD, hydroxide form, 100–200 mesh 1.2 meq./ml. resin in a water packed column the oil was taken up in water and flushed over the column. 800 Milliters was collected off the column. This was partly acidified from pH 12.4 to pH 10 with 15 g. of p-toluenesulfonic acid in water. The solution tended to oil on acidification. This suspension was passed over a column of 300 ml. of resin which had been converted to the tosylate form by washing with 1 l. of 0.4 N p-toluenesulfonic acid solution. A total of 4 l.

eluate was collected. Lyophilization of the eluate of 1½ days left a residue which was taken up in hot ethyl acetate, filtered and evaporated in vacuo. 44 Grams of oil was left which solidified on standing. The material was recrystallized from 300 ml. ethyl acetate to form 36.76 g. N,N-dimethyl-N-n-heptyl-4(4-methoxyphenyl)butylammonium p-toluenesulfonate. M.P. 65°-67° C.

Analysis calc. for $C_{29}H_{47}NO_4S$ Theory: C, 68.87; H, 9.37; N, 2.77; S, 6.34. Found: C, 68.64; H, 9.08; N, 2.80; S, 6.57.

EXAMPLE 74

N,N-Diethyl-N-n-heptyl-4(4-hydroxyphenyl)butylammonium bromide 2.03 Grams of N,N-diethyl-N-n-heptyl-4(4-methoxyphenyl)butylammonium p-toluenesulfonate prepared in Example 73 was dissolved in 1500 ml. water. This was washed over a column of 30 ml. BIO-RAD, hydroxide form, 100–200 mesh, 1.2 meq./ml. resin. 2½ l. Eluate was collected. It was lyophilized for 2 days and an oily residue remained. The oil was placed in a separatory funnel with a water/diethyl ether mixture and extracted three times with diethyl ether. The aqueous fraction was acidified to a pH of 2.0 with 48% hydrobromic acid. It was lyophilized to leave a brown oil with a small amount of white oily layer weighing 1.44 g. This material was refluxed with 10 ml. 48% hydrobromic acid/15 ml. glacial acetic acid for 5 hours. It was cooled and, on evaporation to dryness left an oily material. The oily material was taken up in 50 ml. glacial acetic acid and evaporated to dryness three times. The oil thus formed was stored overnight in a desiccator containing potassium hydroxide and phosphorus pentoxide. 20 Milliters of ethyl acetate was added to the product, from which a precipitate formed and was filtered off and recrystallized from 15 ml. acetone yielding 460 mg. of a material with a m.p. 82°-85° C. This material was redissolved in 15 ml. acetone and recrystallized to yield 349 mg. of N,N-diethyl-N-n-heptyl-4(4-hydroxyphenyl)butylammonium bromide. M.P. 83°-85° C.

Analysis calc. on $C_{21}H_{38}BrNO$ Theory: C, 62.99; H, 9.57; N, 3.50; Br, 19.95. Found: C, 63.22; H, 9.37; N, 3.54; Br, 20.20.

EXAMPLE 75

N,N-Dimethyl-N-(2-phenethyl)phenylbutylammonium bromide

20 Grams of 4-phenyl-n-butylchloride and 48 g. of N-methyl-N-phenethyl-amine was placed in a 100 ml. round bottom flask with boiling chips and heated at 100° C. for 3 days. A solid material formed during heating. An aqueous solution of the material basified with sodium hydroxide was extracted with diethyl ether, which was then extracted with 2 N sulfuric acid and water. The combined sulfuric acid/water solution and washings were made basic with 5 N sodium hydroxide extracted 3 times with diethyl ether and the etheral extracts were washed with saturated sodium chloride. The ether solvent was evaporated in vacuo to yield 64 g. of an oily material. Distillation yielded 27.04 g. of N-methyl-N-(2-phenethyl)phenylbutylamine.

9.0 Grams of N-methyl-N-(2-phenethyl)phenylbutylamine was added to 150 ml. of diethyl ether in a 300 ml. round bottom flask. Methyl bromide gas was bubbled through the mixture untill it was saturated. The mixture was stirred at room temperature for 5 days. A solid material was filtered off and recrystallized in 100 ml. acetone by cooling in a refrigerator. The yield was 8.96 g. of N,N-dimethyl-N-(2-phenethyl)phenylbutylammonium bromide. M.P. 98°-102° C.

Analysis calc. for $C_{20}H_{28}BrN$ Theory: C, 66.29; H, 7.79; N, 3.87; Br, 22.05 Found: C, 66.07; H, 7.72; N, 3.91; Br, 22.16.

EXAMPLE 76

N,N-Dimethyl-N-(3-phenylpropyl)phenylbutylammonium bromide

Phenylbutyric acid chloride and 3-phenylpropylamine were reacted to form the amide which next was reduced with diborane to give N-(3-phenylpropyl)-4-phenylbutylamine. The amine was methylated with formic acid/formaldehyde to form the starting material, N-methyl-N-(3-phenylpropyl)-4-phenylbutylamine. 5.3 Grams of N-methyl-N-(3-phenylpropyl)phenylbutylamine was dissolved in 150 ml. of diethyl ether in a 300 ml. round bottom flask. Methyl bromide gas was bubbled through the mixture until it was saturated. The mixture was stirred at room temperature for 3 days. The solid material which had formed was collected by filtration and crystallized from 100 ml. methyl ethyl ketone and ethyl acetate to yield 5.08 g. of N,N-dimethyl-N-phenylpropyl-phenylbutylammonium bromide. M.P. 81°-83° C.

Analysis calc. for $C_{21}H_{30}BrN$ Theory: C, 67.01; H, 8.03; N, 3.72; Br, 21.23. Found: C, 67.20; H, 8.34; N, 3.49; Br, 21.53.

EXAMPLE 77

N,N-Diethyl-N-n-heptyl-4-(4-chlorophenyl)butylammonium phosphate

960 Grams of 4-Chloro-N,N-diethyl-N-n-heptyl-butylammonium bromide, was divided into four portions of 150–200 g. each, and each portion was dissolved in one liter of water and poured over a 2 lb. column of Dowex 1-X8, hydroxide form, resin. The elution of the quaternary ammonium hydroxide compound with water was continued until the solution was only slightly basic (pH about 8).

The aqueous eluate (2 l.) from the ion exchange column was washed three times with 150 ml. portions of diethyl ether. The aqueous layer was separated and acidified with dilute phosphoric acid to pH 4.5 and then lyophilized to dryness. The crystalline residue was dissolved in 1.5 l. of acetone (hot) and 0.5 l. of diethyl ether was added, whereupon the solution became cloudy. The solution was place in a dry ice-acetone bath and a seed crystal added. The crystalline material was collected by filter suction and washed with fresh diethyl ether to provide 548 g. M.P. 116°-119° C.

Recrystallization from 8 l. of acetone, 1 l. of dichloromethane and 3 l. of diethyl ether afforded 459 g. of N,N-diethyl-N-n-heptyl-4-(4-chlorophenyl)butylammonium phosphate, now known as clofilium.

Analysis calc. for $C_{21}H_{39}NO_4ClP$ (M.W. 435.973) Theory: C, 57.85; H, 9.02; N, 3.21; P, 7.10; Cl, 8.13 Found: C, 57.59; H, 9.21; N, 3.11; P, 6.88; Cl, 8.39.

EXAMPLE 78

N,N-Dimethyl-N-n-heptyl-3(4-chlorophenylpropylammonium p-toluenesulfonate

45 Mililiters of BIO-RAD, hydroxide form, 100–200 mesh, 1.2 meq./ml. resin, were placed in a column and washed with water until neutral. 4.50 Grams of N,N- dimethyl-N-n-heptyl-3-(4-chlorophenyl)propylammonium bromide was dissolved in 300 ml. water and passed through the column. 350 Milliliters of eluate was collected until it was no longer basic. The solution was acidified with 0.2 m. p-toluene sulfonic acid from an initial pH of 11.7 to a final pH of 10.4. Another column packed with 45 ml. of resin was washed until the collected water was neutral. Then the 0.2 m p-toluene sulfonic acid solution was passed over the column until the acid was coming through the column (300 ml.). The column was then washed with water until neutral. Then the aqueous suspension which was at pH of 10.4 was flushed over the column to finish acidifying and 800 ml. of eluate was collected and lyophilized over the week end. A solid residue remained. It was dissolved in ethyl acetate and the insoluble material filtered off. Crystallization from a 300 ml. ethyl acetate solution yielded 4.90 g. N,N-dimethyl-N-n-heptyl-3(4-chlorophenyl-propylammonium p-toluenesulfonate. M.P. 117°–119° C.

Analysis calc for $C_{25}H_{38}ClNO_3S$ Theory: C, 64.15; H, 8.18; N, 2.99; Cl, 7.57; S, 6.85. Found: C, 64.31; H, 7.90; N, 3.16; Cl, 7.68; S, 6.91.

EXAMPLE 79

N,N-Diethyl-N-n-heptyl-3(4-chlorophenyl)propylammonium bromide 7.764 Grams of N-ethyl-N-n-heptyl-3(4-chloro)-propylamine was placed in a 200 ml. round bottom flask. 90 Milliliters of ethyl bromide was added. The mixture was refluxed for 5 days. The ethyl bromide was evaporated off in vacuo leaving an oil which slowly solidified. The material was recrystallized from 400 ml. ethyl acetate with seeding to yield 9.29 g. N,N-diethyl-N-n-heptyl-3(4-chlorophenyl)propylammonium bromide. M.P. 83°–85° C.

Analysis calc. for $C_{20}H_{35}BrClN$ Theory: C, 59.33; H, 8.71; N, 3.46; Cl, 8.76; Br, 19.74. Found: C, 59.37; H, 8.51; N, 3.22; Cl, 8.87; Br, 20.07.

EXAMPLE 80

N,N-Diethyl-N-n-heptyl-4(4-chlorophenyl)butylammonium benzenesulfonate

100 Milliliters of BIO-RAD, hydroxide form, 100–200 mesh, 1.2 meq./ml resin were used for each column. The columns were washed with water until neutral. 9.9 g. N,N-Diethyl-N-n-heptyl-4(4-chlorophenyl)butylammonium bromide was dissolved in 50 ml. water. It was washed over the resin and the eluate collected until the column discharge was neutral again (300 ml.). The above eluate was acidified from pH 12.4 to 10.4 using a 0.2 M. p-toluenesulfonic acid. The solution became cloudy with an oily suspension. This suspension was run over a column of 100 ml. of resin which had been converted from the hydroxide form to the benzene sulfonic acid form. 800 Milliliters eluate was collected and the rest stayed on the column overnight. Three additional 800 ml. lots of eluate were collected. All material collected was lyophilized over the weekend with a resultant residue of oil which had started to solidify. The oil was taken up in ethyl acetate, solids removed by filtration and evaporated in vacuo to yield 11.994 g. of an oil. The oil was then taken up in 100 ml. ethyl acetate chilled in a refrigerator and seeded with crystals. Crystallization occurred overnight to yield 9.325 g. product. M.P. 46°–48° C. The material was again recrystallized in 100 ml. ethyl acetate and yielded 8.82 g. M.P. 47°–49° C.

Analysis calc. for $C_{27}H_{42}ClNO_3S$ Theory: C, 65.36; H, 8.53; N, 2.82; Cl, 7.15; S, 6.46. Found: C, 65.34; H, 8.26; N, 3.14; Cl, 7.23; S, 6.66.

EXAMPLE 81

N,N-Di-n-octyl-N-methyl-4-phenylbutylammonium bromide 5.787 Grams of N,N-Di-n-octyl-4-phenylbutylamine was placed in 150 ml. diethyl ether in a 300 ml. round bottom flask. Methyl bromide gas was bubbled through the mixture until it was saturated. The mixture was stirred at room temperature for 48 hours. Thin layer chromatography at that time showed small amounts of secondary amine. Solids were filtrated from the suspension. Recrystallization from 50 ml. ethyl acetate yielded 5.848 g. N,N-di-n-octyl-N-methyl-4-phenylbutylammonium bromide. M.P. 65°–67° C.

Analysis calc. for $C_{27}H_{50}BrN$ Theory: C, 69.20; H, 10.76; N, 2.99; Br, 17.05. Found: C, 69.25; H, 10.56; N, 3.09; Br, 16.93.

EXAMPLE 82

N,N,N-Triethyl-1-methyl-4-phenylbutylammonium bromide 3.65 Grams of N,N-diethyl-1-methyl-4-phenylbutylamine and 35 ml. ethyl bromide were placed in a 100 ml. round bottom flask and refluxed for 3 days. At the end of refluxing a white percipitate had formed. The mixture was cooled and the excess solvent was evaporated in vacuo leaving an oily semisolid. 50 Milliliters of diethyl ether was added and the solids were removed by filtration. The diethyl ether was evaporated in vacuo leaving 3.135 g. of material which was placed in a 100 ml. round bottom flask and 35 ml. ethyl bromide added and refluxed as above one week. The mixture was cooled and evaporated to dryness, then taken up in 75 ml. diethyl ether and the solid filtered off. The material was recrystallized in 50 ml. methyl ethyl ketone to yield 619 mg. of N,N,N-triethyl-1-methyl-4-phenylbutylammonium bromide. M.P. 123°–125° C.

Analysis calc. for $C_{17}H_{30}BrN$ Theory: C, 62.19; H, 9.21; N, 4.27; Br, 24.34. Found: C, 62.13; H, 9.06; N, 4.29; Br, 24.05.

EXAMPLE 83

N,N-Dimethyl-N-(1-methylheptyl)-4-phenylbutylammonium bromide

4-Phenylbutyryl chloride was reacted with 1-methylheptylamine to provide N-(1-methylheptyl)-4-phenylbutyramide, which, when reduced by reaction with dibroane in tetrahydrofuran, provided N-(1-methylheptyl)-4-phenylbutylamine. The amine so formed was reacted with formic acid and formaldehyde to give N-methyl-N-(1-methylheptyl)-4-phenylbutylamine.

The mixture of 5.07 g. of N-methyl-N-(1-methylheptyl)-4-phenylbutylamine and 150 ml. diethyl ether was saturated with methyl bromide gas. The solution was stirred at room temperature for three days. The precipitate was collected by filtration and recrystallized from ethyl acetate to yield 3.76 g. of N,N-dimethyl-N-(1-methylheptyl)-4-phenyl butylammonium bromide. M.P. 111°–113° C.

Analysis calc. for $C_{20}H_{36}BrN$ Theory: C, 64.85; H, 9.80; N, 3.78; Br, 21.57. Found: C, 64.64; H, 9.65; N, 3.68; Br, 21.45.

EXAMPLE 84

N,N-Diethyl-N-(3-methylbutyl)-4(4-nitrophenyl)-butylammonium bromide 4-(4-Nitrophenyl)butyryl chloride was reacted with 3-methylbutylamine to afford the corresponding amide, which then was reduced by reaction with diborane to provide N-(3-methylbutyl)-4-(4-nitrophenyl)butylamine.

15.4 Grams of sodium carbonate in 70 ml. water was placed in a 500 ml. 3-neck round bottom flask containing 19.183 g. of N-3-methylbutyl-4(4-nitrophenyl)-butylamine in 70 ml. acetone. The mixture was cooled below 30° C. and 11.35 ml. of acetyl chloride in 70 ml. acetone was added dropwise keeping the temperature below 30° C. A precipitate appeared after the addition of the acetyl chloride was complete. The suspension was stirred overnight at room temperature. The acetone was evaporated off in vacuo. The mixture was diluted with 100 ml. water and then was extracted three times with diethyl ether. The etheral extracts were combined, washed once with water, once with 2 N hydrochloric acid, four times with water, and once with water saturated with sodium chloride. The etheral solution was then dried and all solvent removed by evaporation in vacuo to yield 21.81 g. of N-3-methylbutyl-N-acetyl-4(4-nitrophenyl)butylamine.

220 Milliliters of 1 M. diborane in tetrahydrofuran was placed in a 1 l. three neck round bottom flask. The 21.81 g. N-(3-methylbutyl)-N-acetyl-4(4-nitrophenyl)-butylamine prepared above in 100 ml. tetrahydrofuran were added dropwise. The mixture was refluxed overnight. After cooling, 200 ml. 2 N hydrochloric acid was added to decompose excess diborane. The tetrahydrofuran was removed by evaporation. 100 Milliliters of a concentrated hydrochloric acid was added and the mixture refluxed for 45 minutes to decompose the diborane complex. The mixture was cooled, basified with 5 N sodium hydroxide, extracted three times by diethyl ether. The etheral extracts were combined washed once with water and extracted two times with 2 N sulfuric acid. The acidic extracts were basified with 5 N sodium hydroxide, extracted three times with diethyl ether. The etheral extracts were washed with saturated sodium chloride, dried and the solvent removed by evaporation in vacuo to yield 19.82 g. of N-ethyl-N-(3-methylbutyl)-4(4-nitrophenyl)butylamine.

3.383 Grams of N-ethyl-N-(3-methylbutyl)-4(4-nitrophenyl)butylamine and 40 ml. ethyl bromide were added to a 100 ml. round bottom flask and heated at reflux temperature for five days. A solid precipitated out during the reaction. The excess ethyl bromide was evaporated off in vacuo and the residue was recrystallized from 75 ml. methyl ethyl ketone to yield 2.28 g. N,N-diethyl-N-(3-methylbutyl)-4(4-nitrophenyl)-butylammonium bromide. M.P. 114°–116° C.

Analysis calc. for $C_{19}H_{33}BrN_2O_2$ Theory: C, 56.85; H, 8.29; N, 6.98; Br, 19.91. Found: C, 56.62; H, 8.11; N, 6.69; Br, 19.62.

EXAMPLE 85

N,N-Diethyl-N-n-hexyl-3-phenylpropylammonium bromide 5.21 Grams of N-ethyl-N-n-hexyl-3-phenylpropylamine was placed in a 200 ml. round bottom flask. 100 Milliliters of ethyl bromide was added. The mixture was refluxed five days. Excess ethyl bromide was removed by evaporation in vacuo leaving as an oil N,N-diethyl-N-n-hexyl-3-phenylpropylammonium bromide.

EXAMPLE 86

N,N-Diethyl-N-n-hexyl-3-phenylpropylammonium p-toluenesulfonate

Two columns were packed using 40 ml. BIO-RAD, hydroxide form, 100–200 mesh, 1.2 meq./ml. resin. One column was washed with water until it was neutral. The N,N-diethyl-N-n-hexyl-3-phenylpropylammonium bromide prepared in Example 85 was taken up in 200 ml. of water and washed over a column, converting the bromide to hydroxide. This aqueous column was acidified to a pH of 7 with 0.2 N p-toluenesulfonic acid. The other column was washed with 0.2 N p-toluenesulfonic acid solution until acid wash was coming off. Then it was washed with water until neutral. The partly acidified aqueous solution was then passed over the tosylate column. About 1 l. water was collected. It was lyophilized. The solid was recrystallized in 50 ml. ethyl acetate to yield 8.10 g. of N,N-diethyl-N-n-hexyl-3-phenylpropylammonium p-toluenesulfonate. M.P. 61°–63° C.

Analysis calc. for $C_{26}H_{41}NSO_3$ Theory: C, 69.76; H, 9.23; N, 3.13; S, 7.16. Found: C, 69.84; H, 8.96; N, 2.92; S, 7.22.

EXAMPLE 87

N,N-Diethyl-N-n-heptyl-3-phenylpropylammonium p-toluenesulfonate 5.302 Grams of N-ethyl-N-n-heptyl-3-phenylpropylamine and 50 ml. ethyl bromide were placed in 100 ml. round bottom flask. The mixture was refluxed for 6 days. Excess ethyl bromide was removed by evaporation in vacuo leaving an oily material. The material was crystallized from 150 ml. of ethyl acetate containing a trace of acetone to yield 6.35 g. of N,N-diethyl-N-n-heptyl-3-phenylpropylammonium bromide. M.P. 60°–62° C. The material was recrystallized a second time in ethyl acetate with a trace of acetone and allowed to stand at room temperature to yield 3.34 g. N,N-diethyl-N-n-heptyl-3-phenylpropylammonium bromide. M.P. 65°–68° C.

Two columns were packed using 10 ml. BIO-RAD, hydroxide form, 100 to 200 mesh, resin. One of the columns was washed with water until the water wash was neutral. 5.387 Grams of N,N-diethyl-N-n-heptyl-3-phenylpropylammonium bromide was dissolved in water and washed over the resin to convert it to the hydroxide form. The eluate was collected until it was no longer basic. The eluate then was acidified to pH 6 with 0.2 N p-toluenesulfonic acid solution. The other column was washed with 0.2 N p-toluenesulfonic acid until acid wash water was comming through. The column was washed with water until neutral. The above partially acidified solution was then washed over this tosylate column. 500 ml. of wash water was collected. It was lyophilized overnight to give a semisolid material. The material was recrystallized in 40 ml. ethyl acetate and yielded 2.16 g. of N,N-diethyl-N-n-heptyl-3-phenylpropylammonium p-toluenesulfonate. M.P. 74°–76° C.

Analysis calc. for $C_{27}H_{43}NSO_3$ Theory: C, 70.24; H, 9.39; N, 3.03; S, 6.94. Found: C, 70.01; H, 9.15; N, 2.84; S, 6.93.

EXAMPLE 88

N,N,N-Trimethyl-3-(4-nitrophenyl)propylammonium bromide 1.12 Grams of N,N-dimethyl-3(4-nitrophenyl)-propylamine was added to 150 ml. diethyl ether in a round bottom flask. Methylbromide was bubbled through the mixture until it was saturated. The mixture was stirred at room temperature for two days. The solids were filtered off and recrystallized from 50 ml. isopropanol to yield 1.49 g. M.P. 180°-181° C.

Analysis calc. for $C_{12}H_{19}BrN_2O_2$ Theory: C, 47.54; H, 6.32; N, 9.24 Br, 26.35 Found: C, 47.29; H, 6.07; N, 9.13 Br, 26.66.

EXAMPLE 89

Formulation for oral administration

| | |
|---|---|
| N,N—Diethyl-N—n-propyl-4-(4-(4-chlorophenyl)butylammonium phosphate | 300 mg |
| Lactose | 300 mg |
| Corn starch | 300 mg |
| Corn starch paste | 50 mg |
| Calcium stearate | 5 mg |
| Dicalcium phosphate | 45 mg |

The active ingredient, clofilium, is mixed uniformly with the corn starch, lactose and dicalcium phosphate. The corn starch paste is prepared as a 10 percent aqueous paste and is blended into the mixture to uniformity. The mixture is then blended with the calcium stearate and then compressed into tablets, preferably such that each tablet contains about 10 mg. of clofilium. Such tablets are administered, at the rate of 1 to about 3 per day, to a subject weighing about 70 kg. and in need of therapeutic or prophylactic treatment for re-entrant arrhythmias.

EXAMPLE 90

Preparation for oral suspension

| | |
|---|---|
| N—Ethyl-N—methyl-N—n-pentyl-4-(4-nitrophenyl)butylammonium bromide | 500 mg |
| Sorbitol solution (70% N.F.) | 40 mg |
| Sodium benzoate | 150 mg |
| Lactose | 10 mg |
| Cherry flavor | 50 mg |
| Water | 100 ml |

The above ingredients are combined such that each ml. of syrup contains 5 mg. of active ingredient. Administration of about 1 to about 5 ml. of the syrup each day will help prevent sudden death due to heart failure.

EXAMPLE 91

Formulation for parenteral administration

| | |
|---|---|
| N,N—diethyl-N—n-hexyl-3-(4-nitrophenyl)propylammonium acetate | 10 mg |
| isotonic saline | 100 mg |

A solution of the above active ingredient in isotonic saline is administered intravenously to a patient suffering from ventricular fibrillation and in need of treatment. Such treatment can, if desired, be in conjunction with an external electrical device designed to aid defibrillation.

We claim:

1. A compound having the general formula

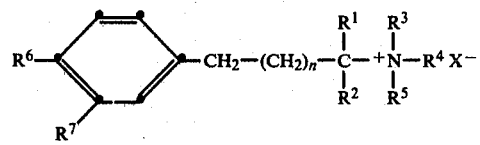

wherein:
n is 1 or 2;
$R^1$ is hydrogen or $C_1$-$C_2$ alkyl;
$R^2$ is hydrogen or $C_1$-$C_3$ alkyl;
$R^3$ is $C_1$-$C_4$ alkyl or phenyl $C_1$-$C_4$ alkyl;
$R^4$ and $R^5$ taken together with the adjacent nitrogen to which they are attached complete a heterocyclic ring having 4 to 7 carbon atoms;
$R^6$ and $R^7$ independently are hydrogen, hydroxy, halogen, nitro, $C_1$-$C_3$ alkoxy, or $C_1$-$C_3$ alkyl, provided that at least one of $R^6$ and $R^7$ is hydrogen, and
X is a therapeutically acceptable anion.

2. The compound of claim 1 wherein $R^3$ is $C_1$-$C_4$ alkyl and $R^6$ and $R^7$ independently are hydrogen, halogen, nitro, $C_1$-$C_3$ alkoxy, or $C_1$-$C_3$ alkyl.

3. The compound of claim 2 wherein n is 1.

4. The compound of claim 1 wherein $R^6$ is halogen or nitro.

5. The compound of claim 1 wherein n is 2 and $R^6$ is halogen or nitro.

6. The compound of claim 1 wherein $R^1$ is $C_1$-$C_2$ alkyl and $R^2$ is hydrogen.

7. The compound according to claim 1 which is N-methyl-N-(4-phenylbutyl)hexahydroazepinium bromide.

8. The compound according to claim 1 which is N-methyl-N-(4-phenylbutyl)-tetrahydropyrrolium bromide.

9. The compound according to claim 1 which is N-methyl-N-(4-phenylbutyl)piperidinium methanesulfonate.

10. A method of treating re-entrant arrhythmias in humans suffering from such arrhythmias and in need of treatment or in humans suspected of developing a re-entrant arrhythmia comprising administering to such subject an antiarrhythmically effective dose of a compound of claim 1.

11. The method according to claim 10 employing a compound wherein $R^3$ is $C_1$-$C_4$ alkyl and $R^6$ and $R^7$ independently are hydrogen, halogen, nitro, $C_1$-$C_3$ alkoxy, or $C_1$-$C_3$ alkyl.

12. A pharmaceutical formulation for the treatment of re-entrant arrhythmias in humans comprising as active ingredient an antiarrhythmic amount of a quaternary ammonium salt of claim 1 in combination with one or more pharmaceutically acceptable diluents or carriers therefor.

13. The formulation of claim 12 employing a compound wherein $R^3$ is $C_1$-$C_4$ alkyl, and $R^6$ and $R^7$ independently are hydrogen, halogen, nitro, $C_1$-$C_3$ alkoxy or $C_1$-$C_3$ alkyl.

* * * * *